(12) United States Patent
Martin et al.

(10) Patent No.: US 7,179,800 B2
(45) Date of Patent: Feb. 20, 2007

(54) CANNABINOIDS

(75) Inventors: Billy R. Martin, Richmond, VA (US);
Raj K. Razdan, Gloucester, MA (US)

(73) Assignee: Virginia Commonwealth University, Richmond, VA (US)

( * ) Notice: Subject to any disclaimer, the term of this patent is extended or adjusted under 35 U.S.C. 154(b) by 305 days.

(21) Appl. No.: 10/413,539

(22) Filed: Apr. 15, 2003

(65) Prior Publication Data

US 2005/0159449 A1 Jul. 21, 2005

Related U.S. Application Data

(63) Continuation-in-part of application No. PCT/US02/19569, filed on Jun. 20, 2002.

(60) Provisional application No. 60/375,012, filed on Apr. 25, 2002.

(51) Int. Cl.
*A61K 31/33* (2006.01)
*C07C 39/12* (2006.01)

(52) U.S. Cl. .................... 514/183; 568/731

(58) Field of Classification Search ............ 549/78; 568/743, 747, 731; 514/438, 719, 721, 729, 514/736, 183
See application file for complete search history.

(56) References Cited

U.S. PATENT DOCUMENTS

| 4,092,344 | A |   | 5/1978  | Matsumoto |         |
| 4,102,902 | A |   | 7/1978  | Archer et al. |     |
| 4,282,248 | A | * | 8/1981  | Mechoulam et al. | 514/511 |
| 4,707,559 | A | * | 11/1987 | Mechoulam et al. | 568/644 |
| 4,758,597 | A | * | 7/1988  | Martin et al. | 514/729 |

(Continued)

FOREIGN PATENT DOCUMENTS

WO  WO 01/028329 A  4/2001

(Continued)

OTHER PUBLICATIONS

Drake, David J. et al; "Classical/Nonclassical Hybrid Cannabinoids: Southern Aliphatic Chain-Functionalized C-6β Methyl, Ethyl, and Propyl Analogues"; J. Med. Chem., No. 41, 1998, pp. 3596-3608, XP-002217966.

(Continued)

*Primary Examiner*—Samuel Barts
*Assistant Examiner*—Kellette Gale
(74) *Attorney, Agent, or Firm*—Nixon & Vanderhye

(57) ABSTRACT

Compounds of the formula:

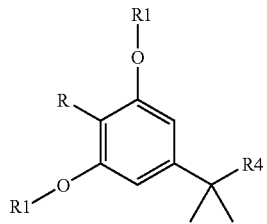

wherein R, R1 and R4 are defined in the specification, and pharmaceutically acceptable salts, esters and tautomers thereof, having activity at peripheral cannabinoid receptors, commonly designated the CB2 receptor class. The compounds are useful for therapy, especially in the treatment of pain, inflammation and autoimmune disease.

11 Claims, 4 Drawing Sheets

Δ⁹-THC

CP 55,950

Cannabidiol

HU-308

U.S. PATENT DOCUMENTS 5,434,295 A     7/1995    Mechoulam et al.
6,274,635 B1 *   8/2001    Travis ....................... 514/718
6,563,009 B1 *   5/2003    Kunos et al. ............... 568/743
6,630,507 B1 * 10/2003    Hampson et al. ........... 514/454

FOREIGN PATENT DOCUMENTS

WO       WO 01/95899 A2    12/2001

OTHER PUBLICATIONS

Gareau, Yves, et al; "Structure Activity Relationships of Tetrahydrocannabinol Analogues on Human Cannabinoid Receptors"; Biorg. Med. Chem. Lett., vol. 6, No. 2; 1996; pp. 189-194, XP004135106.

Baek, Seung-Hwa, et al; "Boron Trifluoride Etherate on Alimina—A Modified Lewis Acid Reagent. An Improved Synthesis of Cannabidiol"; Tetrahedron Letters, Elsevier Science Publ.; Amsterdam, NL, vol. 8, No. 26, 1985; pp. 1083-1086; XP001095309.

Baek, Seung-Hwa; et al; "Boron Trifluorideetherate on Alumina—A Modified Lewis Acid Reagent . . . Diacetate Derivatives"; Bull. Korean Chem. Soc., vol. 15, No. 6, 1994, pp. 507-508, XP00222251.

Chemical Abstracts Service, Columbus, OH; Baek, Seung-Hwa; "Simplified cannabidiols. Part 1. Boron trifluoride-diethyl ether on alumina: a modified Lewis acid reagent . . . allylic alcohols"; Database accession No. 122:132675; XP002222552; J. Chem. Research, 1994, pp. 2549-2561.

* cited by examiner (a) n-BuLi, hexane/THF, 0 °C, 1 h; ketone, THF, 0 °C, 0.5 h to 23 °C, 18 h, 80–90%; (b) CF$_3$COOH, ET$_3$SiH, CH$_2$Cl$_2$, 23 °C, 1 h; (c) BBr$_3$/CH$_2$Cl$_2$, 0 °C to 23 °C, 18 h; Overall yield (a to c), ~50–80%; (d) 10% HCl, ether/THF (5:4), 23 °C, 0.5 h; yield O-2115 (41%) and O-2114 (19%); (e) m-chloroperbenzoic acid, CH$_2$Cl$_2$/H$_2$O (4:3), 23 °C, 10 min; (f) NaBH$_4$, CH$_2$Cl$_2$/MeOH (1:1), 23 °C, 18 h, ~90%; Overall yield (e and f), ~50%.

Cannabinoid Receptor (CB$_2$) Selective Resorcinol Derivative

CANNABINOIDS

This application is a Continuation-In-Part of PCT International Application No. PCT/US02/19569 filed Jun. 20, 2002 which designated the U.S., and claimed the benefit of U.S. Provisional Application Ser. No. 60/375,012 filed Apr. 25, 2002, the contents of which are hereby incorporated by reference in this application.

BACKGROUND AND SUMMARY OF THE INVENTION

The present invention relates to novel compounds that have activity at peripheral cannabinoid receptors, commonly designated the CB2 receptor class. Particularly these compounds are more specific for said CB2 receptor class than many other compounds active on cannabinoid receptors CB1 and CB2.

At least five different classes of cannabinoids have been identified: traditional tricyclic tetrahydrocannabinoids, such as $\Delta^9$-tetrahydrocannabinoid ($\Delta^9$-THC), synthetic bicyclic cannabinoids such as CP55,940 (see Little et al (1988)), aminoalkylindole such as WIN55,212 (see D'Ambra et al (1992)), endocannabinoid such as anandamide (see Devane et al (1992)), and pyrazole antagonists such as SR141716A (see Rinaldi-Carmona (1994)). Although the chemical structure of these cannabinoids differ markedly, all of them contain at least one oxygen that is hypothesized to be involved in binding of these drugs to brain cannabinoid (CB1) receptors.

$\Delta^9$-THC, the primary psychoactive constituent of the marijuana plant, and other tetrahydrocannabinols contain two oxygens; a phenolic hydroxyl at position 1 and an oxygen pyran ring on the opposite side of the molecule. The hydroxyl oxygen interacts with the CB1 receptor through hydrogen bonding with a lysine residue (Lys 192) (see Song and Bonner (1996)). The role of the oxygen of the benzopyran substituent of $\Delta^9$-THC is less clear; however it is known that opening of the pyran ring as in CP55,940 does not eliminate binding or in vivo activity (See Little et al (1988)). In the absence of a phenolic hydroxyl, as in 1 deoxyanalogs of $\Delta^8$-THC, orientation of the cannabinoid molecule with respect to the CB1 receptor may be inverted and the pyran oxygen may substitute as a substrate for hydrogen bonding with Lys 192 (see Huffman et al (1996), (1999)).

In contrast to the high binding affinity of CP55,940 and other similar pyran-ring open analogs the natural product cannabidiol is also a pyran-ring open compound yet does not bind to CB1 or CB2 receptors nor does it have a cannabinoid profile of effects in vivo Even the 1',1'-dimethylheptyl analog of cannabidiol binds very poorly to the CB1 receptor. With this in mind the present inventors have studied the structural activity relationship of resorcinol derivatives which could be considered as cannabidiol analogs.

During this study, Hanu et al (1999) published synthesis and activity of HU-3-8, a dimethoxyresorcinol derivative that is a CB2 selective agonist. The transmembrane regions of CB2 receptors, which are involved in ligand recognition, exhibit 68% homology with those of CB1 receptors (see Munro et al (1993)). Showalter et al (1996) reported a high positive correlation (r=0.82) between binding affinities at these two cannabinoid receptors for cannabinoids in various classes; thus some of the structural features that enhance affinity for CB1 also enhance affinity for CB2.

Addition of a 1',1'-dimethyl group to the lipophilic C3 side chain of $\Delta^8$-THC results in higher affinity for both receptors as compared to a nonbranched chain of identical length. Synthesis of a series of $\Delta^8$-THC analogs in which the phenolic hydroxyl at position 1 was removed (deoxy-$\Delta^8$-THC analogs) or was replaced with a methoxyl resulted in analogs with selectivity for CB2 receptors (see Gareau et al (1996); Huffman et al (1996)(1999)). Incorporation of an oxygen into a fourth ring attached at C1 also increased CB2 selectivity, suggesting differences in the interaction of oxygen in the binding pockets of CB1 and CB2 (see Reggio et al (1997)).

The present inventors have now provided bicyclic resorcinols in which the core chemical structure contains two hydroxyl or alkoxyl substituents positioned with a single intervening carbon in a benzene ring with a second cyclic substituent attached at the intermediate carbon.

In a first aspect of the present invention are provided novel compounds of general formula I

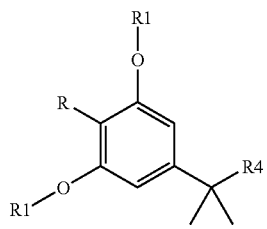

wherein:

R is selected from the group consisting of optionally substituted carbocyclic and heterocyclic rings;

R1 is independently selected at each occurrence from the group consisting of hydrogen and $C_{1-6}$ alkyl;

R4 is selected from the group consisting of optionally substituted $C_{1-10}$ alkyl or alkenyl;

and pharmaceutically acceptable salts, esters and tautomers thereof.

Preferred compounds of the invention have R as optionally substituted aryl, e.g. phenyl, cyclohexyl, cycloheptyl, cyclohexenyl, cyclopentyl, tetrahydrothiopyranyl, methandienyl, cycloheptyl, adamantanyl, tetrahydrothiophen-3-yl, 1-alkyl-piperidinyl, 4-aryl-cyclohexyl, 3,3-dialkylcyclohexyl, tetrahydropyranyl, 1-cyclohexanolyl, 1-4-dioxospirocycloalkyl, and cyclohex-3-enonyl.

Preferred compounds of the invention have R1 as hydrogen or methyl.

Preferred compounds of the invention have R4 as linear, $C_{3-8}$ alkyl, eg. $C_{5-7}$ alkyl, e.g., butyl, pentyl or hexyl.

Still more preferred compounds of the present invention have a group R6 at the 1-position of the ring R4 which is selected from the group consisting of hydroxyl and $C_{1-3}$ alkoxyl, but more preferably more preferably hydroxyl. More preferred groups R4 are optionally substituted cyclic alcohols such as cyclopentan-1-ol, cyclohexan-1-ol, cyclohexan-1-ol and equivalent 1-ols of the other rings cited above as suitable for use as R4.

Substituents on the alkyl or alkenyl group R4 may generally be selected from electron withdrawing or electron donating groups such as is known in the art of cannabinoid chemistry, Conveniently, other than the hydroxyl or alkoxyl group at the 1-position of the ring R4, these will be selected from $C_{1-6}$ alkyl and halo, but may be groups such as phenyl and heterocyclic rings.

A preferred group of novel compounds of the first aspect of the invention are of general formula II

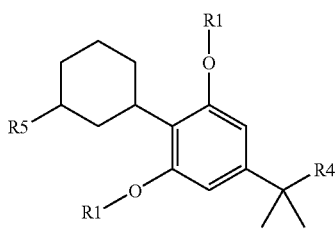

wherein R1 and R4 are as described for formula I and R5 is $C_{1-6}$ alkyl, more preferably methyl or ethyl. More preferably R1 is hydrogen or methyl, more preferably hydrogen. All isomers of compounds of formula II are of interest, but particularly preferred are isomer A and isomer B and the 3R-alkylcyclohexyl compounds, particularly compounds of formula

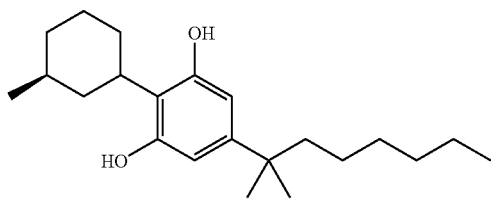

2-(3-methylcyclohexyl)-5-(1,1'-dimethylheptyl)-resorcinol isomer A (O-1797)

2-(3-methylcyclohexyl)-5-(1,1'-dimethylheptyl)-resorcinol isomer B (O-1798)

2-(3R-methylcyclohexyl)-5-(1,1'-dimethylheptyly)-resorcinol (O-1826).

Still more preferred are the hydroxyl derivatives of these compounds which are the 1-{4-(1,1-Dimethyl-heptyl)-2,6-dimethoxy-phenyl}-3-methyl-cyclohexanol compounds O-2137 and its racemates O-1966 and O-1967.

A second aspect of the present invention provides a method of treating a patient in need of therapy for pain, particularly peripheral pain and/or inflammation or autoimmune associated disease comprising administering to that patient a therapeutically effective amount of a compound of formula I, more preferably of formula II. Such amount will typically be administered in a pharmaceutically acceptable carrier, such as is well known in the art.

A third aspect of the present invention provides a composition comprising a compound of formula I or II together with a pharmaceutically acceptable carrier and/or excipient. The composition should be sterile and, if intended for injection, non-pyrogenic.

Administration of the aforementioned compounds of the invention or a formulation thereof need not be restricted by route. Options include enteral (for example oral and rectal) or parenteral (for example delivery into the nose or lung or injection into the veins, arteries, brain, spine, bladder, peritoneum, muscles or subcutaneous region). The treatment may consist of a single dose or a plurality of doses over a period of time. The dosage will preferably be determined by the physician but may be between 0.01 mg and 1.0 g/kg/day, for example between 0.1 and 500 mg/kg/day. In terms of dose per square meter of body surface, the compound can be administered at 1.0 mg to 1.5 g per $m^2$ per day, for example 3.0–200.0 mg/$m^2$/day.

Whilst it is possible for a compound of the invention to be administered alone, it is preferable to present it as a pharmaceutical formulation, together with one or more acceptable carriers and/or excipients. The carrier(s) and/or excipients must be "acceptable" in the sense of being compatible with the compound of the invention and not deleterious to the recipients thereof.

The formulations may conveniently be presented in unit dosage form and may be prepared by any of the methods well known in the art of pharmacy. A unit dosage form may comprise 2.0 mg to 2.0 g, for example 5.0 mg to 300.0 mg of active ingredient. Such methods include the step of bringing into association the active ingredient, i.e., the compound of the invention, with the carrier and/or excipients which constitute one or more accessory ingredients. In general the formulations are prepared by uniformly and intimately bringing into association the active ingredient with liquid carriers or finely divided solid carriers and/or excipients and/or two or all of these, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropyl-methyl cellulose), lubricant, inert diluent, preservative, disintegrant (e.g. sodium starch glycollate, PVP, cross-linked povidone, cross-linked sodium carboxymethyl cellulose), surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Formulations suitable for parenteral administration include aqueous and non-aqueous sterile injection solutions which may contain anti-oxidants, buffers, bacteriostats and solutes which may render the formulation isotonic with the blood of the intended recipient, and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

In a fourth aspect of the present invention there is provide a compound of the first aspect of the invention for use in therapy.

In a fifth aspect of the present invention there is provided the use of a compound of the first aspect of the invention for the manufacture of a medicament for the treatment of a pain, inflammation and autoimmune disease.

BRIEF DESCRIPTION OF THE DRAWINGS

The present invention will now be described further by reference to the following non-limiting examples and Figures. These are provided for the purpose of illustration only and other examples falling within the scope of the claims will occur to those skilled in the art in the light of these. All literature references cited herein are incorporated by reference.

DETAILED DESCRIPTION OF THE INVENTION

Subjects

Male ICR mice (25–32 g), obtained from Harlan (Dublin, Va.), were housed in groups of five. All animals were kept in a temperature-controlled (20–22° C.) environment with a 12-hour light-dark cycle (lights on at 7 a.m.). Separate mice were used for testing each drug dose in the in vivo behavioral procedures. Brain tissue for binding studies was obtained from male Sprague-Dawley rats (150–200 g) purchased from Harlan Laboratories (Dublin, Va.).

Apparatus

Measurement of spontaneous activity in mice occurred in standard activity chambers interfaced with a Digiscan Animal Activity Monitor (Omnitech Electronics, Inc., Columbus, Ohio). A standard tail-flick apparatus and a digital thermometer (Fisher Scientific, Pittsburgh, Pa.) were used to measure antinociception and rectal temperature, respectively Compounds Resorcinols were synthesized in our labs (Organix, Inc., Woburn, Mass.) according to the procedure specified below and were suspended in a vehicle of absolute ethanol, Emulphor-620 (Rhone-Poulenc, Inc., Princeton, N.J.), and saline in a ratio of 1:1:18. Drugs were administered to the mice intravenously (i.v.) in the tail vein at a volume of 0.1 ml/10 g.

Figure 1:
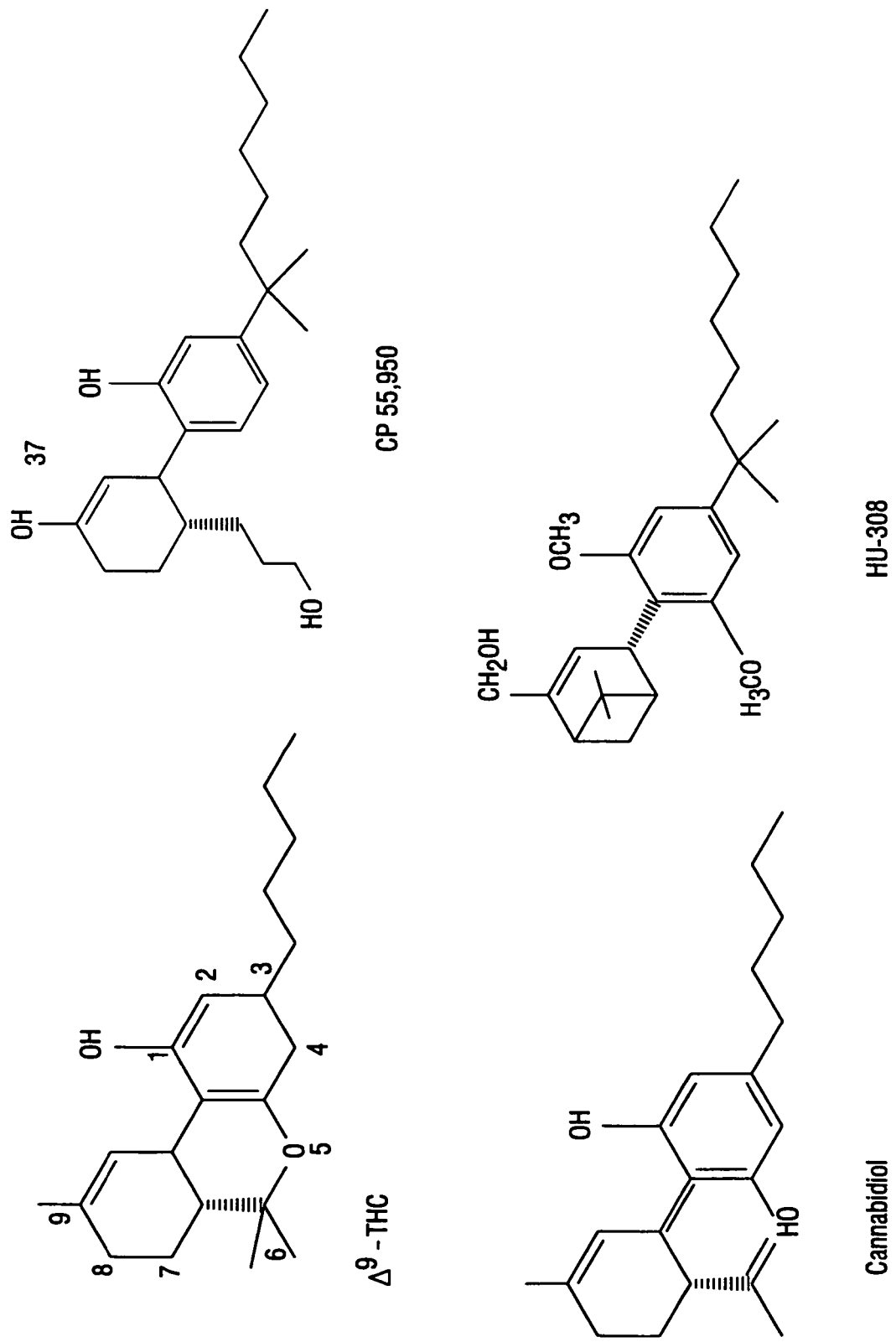
FIG. 1 shows Chemical structures of $\Delta^9$-THC, CP 55,940, and cannabidiol.
Figure 2:
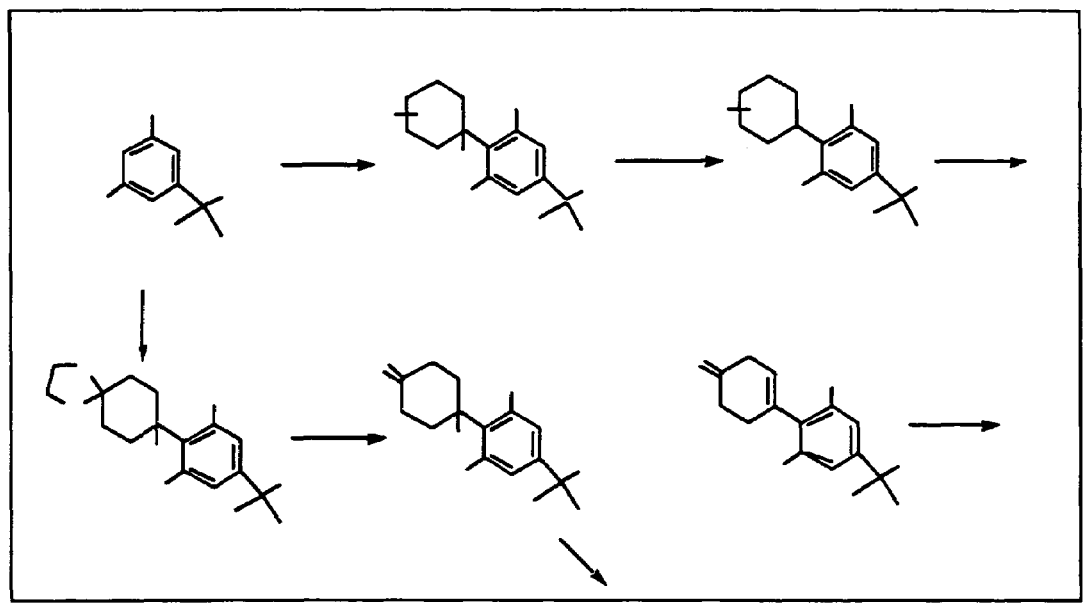
FIG. 2 shows a scheme for synthesis of resorcinol analogs.
Figure 3:
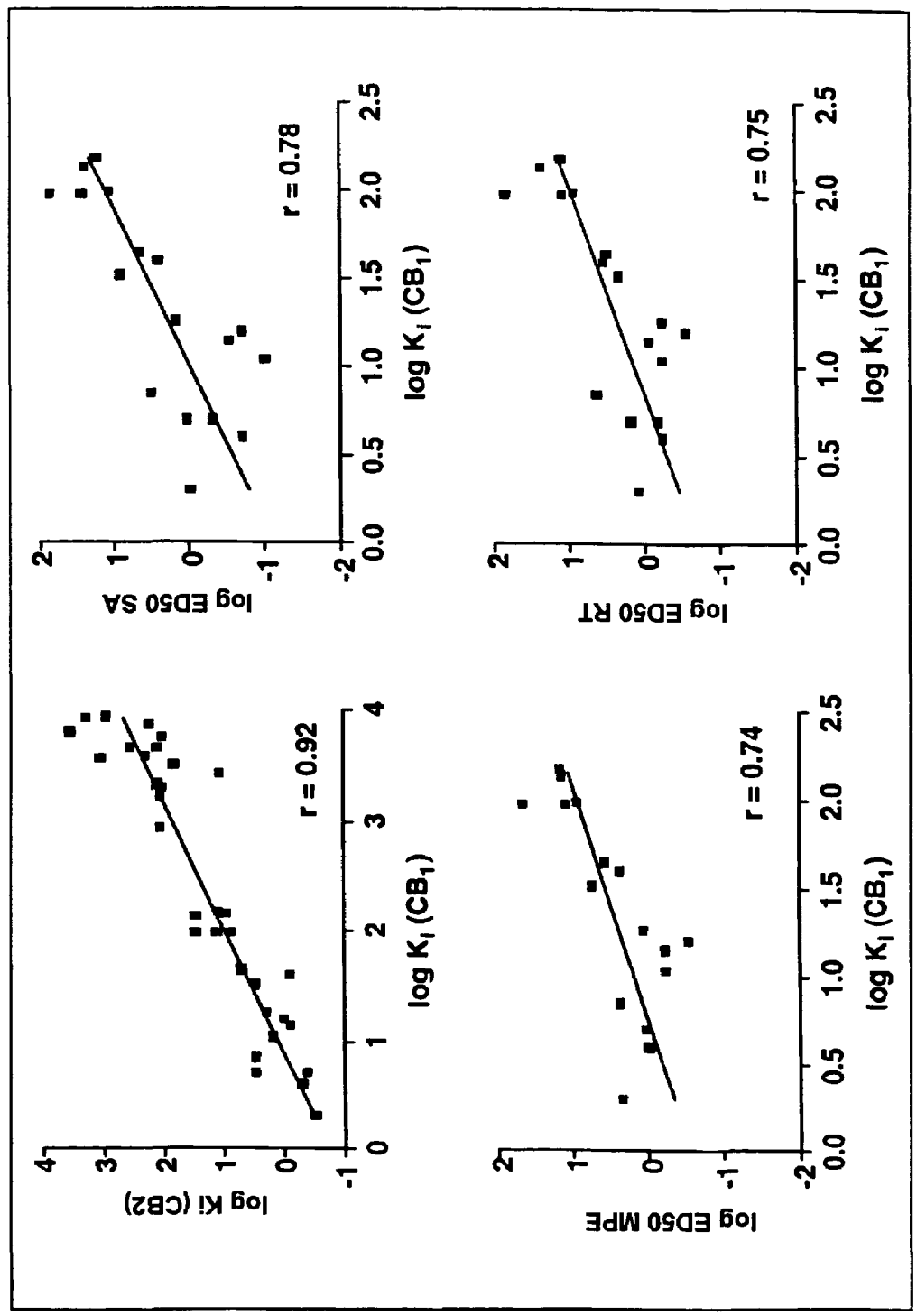
FIG. 3 shows scatterplots and regression lines of log $CB_1$ $K_i$ plotted against log $CB_2$ $K_i$ (top left panel) and log $ED_{50}$ for each of the three in vivo tests (SA=spontaneous activity, top right panel; MPE=% maximum possible antinociceptive effect, bottom left panel; RT=change in rectal temperature, bottom right panel)
Figure 4:
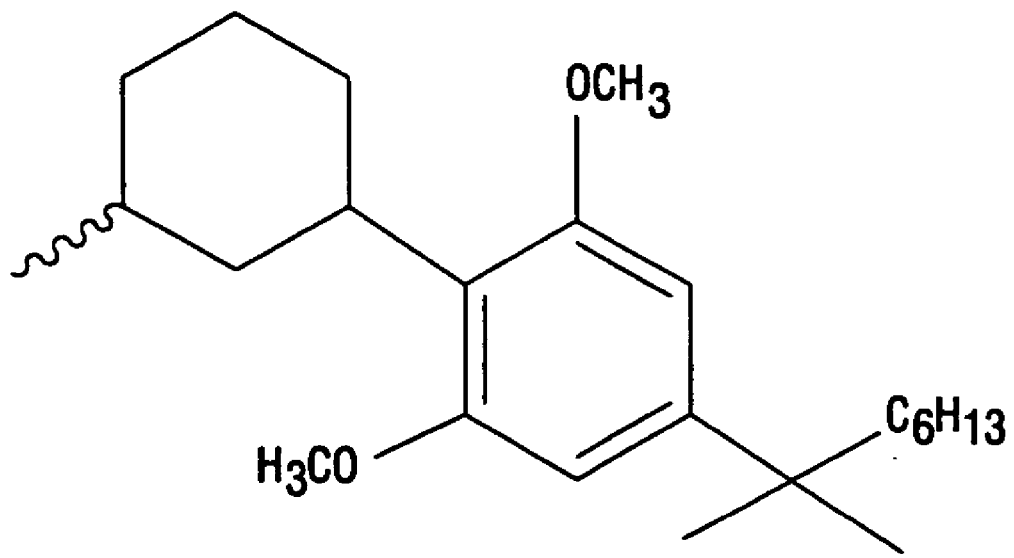
FIG. 4 shows a cannabinoid receptor ($CB_2$) selective resorcinol derivative.

Analogs O-1376 and O-1532 listed in Table 1 were synthesized as previously described (Mahadevan et al., 2000 incorporated herein by reference—see bibliography herein). Analog O-1601 was synthesized from 1-deoxy-9-carbomethoxy cannabinol DMH analog (Mahadevan et al., 2000) by lithium/liquid ammonia reduction as described[1] for the preparation of O-1376. The compounds listed in Tables 2 and 3 were prepared using a three step sequence (FIG. 1). The 2-lithio derivative of 1, 3-dimethoxy-5-(1',1'-dimethylheptyl) resorcinol (1) was prepared using n-BuLi/hexane in THF. It was condensed with the appropriate ketone to give the tertiary alcohol 2, which on treatment with trifluoroacetic acid/$Et_3SiH$ gave the dimethoxy precursors 3. Demethylation[2] with $BBr_3/CH_2Cl_2$ gave the target compounds (Crocker et al., 1999 incorporated herein by reference). The general procedure is illustrated in FIG. 2 and described below.

To a solution of the resorcinol 1, (5 mmol) in 25 ml of dry THF was added a 2.5 M solution of n-BuLi in hexane (5.5 mmol) at 0° C. with stirring/$N_2$. After additional stirring for 1 h at 0° C., added a solution of the ketone (7.5 mmol) in 3 ml of dry THF all at once. The solution was stirred for 0.5 h at 0° C. and then at 23° C. for 18 h. The reaction was worked up by the addition of sat $NH_4Cl$ solution and extracted with ether. After washing ($H_2O$) and drying ($Na_2SO_4$) the solvent was evaporated to give the crude tertiary alcohol 2, which was used as such in the subsequent reaction. A solution of the tertiary alcohol 2 (5 mmol) in 10 ml of dry $CH_2Cl_2$ was treated with $CF_3COOH$ (27.5 mmol) followed by $Et_3SiH$ (12.5 mmol). The solution was stirred/$N_2$ for 1 h or more (followed by TLC) and then quenched by the addition of sat $NaHCO_3$ solution. The organic layer was separated and after washing ($H_2O$) and drying gave the crude dimethoxy precursor 3 of the target compound. This material was used as such for the demethylation step. Treatment of 3, as a solution in dry $CH_2Cl_2$ at 0° C., with 3 equivalents of 1 N $BBr_3$ solution in $CH_2Cl_2$, using the standard procedure and work up[2]. gave the crude target compound, which was purified by chromatography, generally using hexane/ethyl acetate mixtures. In the case of O-1662 (Table 2), the corresponding tertiary alcohol 2 on treatment with $CF_3COOH/Et_3SiH$ gave the unsaturated compound (dehydrated but not reduced) which on catalytic reduction ($PtO_2/C/H_2$) in acetic acid gave the desired dimethoxy precursor 3. The final compound was purified by chromatography using 5% $Et_3NH_2$/EtOAc mixture. The unsaturated analog O-1423 (Table 2) was prepared by treatment of the corresponding tertiary alcohol 2 with $CF_3COOH$ alone in $CH_2Cl_2$ followed by demethylation. In Table 3, compounds O-1797-A and O-1798-B were diastereomeric mixtures and showed as two distinct spots in TLC which were separated by column chromatography, whereas O-1657 was a sample of the mixture of diastereomers O-1797-A and O-1798-B. The dimethoxy compounds listed in Tables 4 and 5 were prepared (FIG. 2) from 1 and the appropriate ketones using BuLi, as in the preparation of 2, and isolating and purifying the compounds by chromatography (ethyl acetate/hexane mixtures). Deprotection of O-2092 was carried out by treatment with 10% HCl in a ether/THF (5:4) mixture for 0.5 h at 23° C. to give a mixture of O-2115 (major) and the dehydrated compound O-2114 (minor). Sodium borohydride reduction of O-2115 furnished a mixture of diastereomeric compounds which were separated by chromatography to give the target compounds O-2116-A and O-2117-B. Similarly O-1966-A and O-1967-B were separated from a diastereomeric mixture by chromatography. Epoxidation of O-2114 followed by $NaBH_4$ reduction gave the target compound O-2122. In the preparation of O-2090 the corresponding diethoxy resorcinol derivative of 1 was used in place of 1. All compounds showed appropriate $^1$HNMRs (Jeol Eclipse 300 MHz) and were characterized on the basis of their $^1$HNMRs, TLC, and elemental analyses.

Mouse Behavioral Procedures

Prior to testing in the behavioral procedures, mice were acclimated to the experimental setting (ambient temperature 22–24° C.) overnight. Pre-injection control values were determined for rectal temperature and tail-flick latency (in sec). Five min after i.v. injection with drug or vehicle, mice were placed in individual activity chambers and spontaneous activity was measured for 10 min Activity was measured as total number of interruptions of 16 photocell beams per chamber during the 10-min test and expressed as % inhibition of activity of the vehicle group. Tail-flick latency was measured at 20 min post-injection. Maximum latency of 10 sec was used. Antinociception was calculated as percent of maximum possible effect {% MPE=[(test−control latency)/(10−control)]×100}. Control latencies typically ranged from 1.5 to 4.0 sec. At 30 min post-injection, rectal temperature was measured This value was expressed as the difference between control temperature (before injection) and temperatures following drug administration (° C.). Different mice (n=5–6 per dose) were tested for each dose of each compound. Each mouse was tested in each of the 3 procedures.

$CB_1$ Binding Procedure

The methods used for tissue preparation and binding have been described previously (Compton et al., 1993) and are similar to those described by Devane et al. (1988). All assays, as described briefly below, were performed in triplicate, and the results represent the combined data from three to six individual experiments.

Following decapitation and rapid removal of the brain, whole brain was homogenized and centrifuged. The resulting pellet was termed $P_1$. The supernatant was saved and combined with the two subsequent supernatants obtained from washing of the $P_1$ pellet. The combined supernatant fractions were centrifuged, resulting in the $P_2$ pellet. After further incubation and centrifuging, this pellet was resuspended in assay buffer to a protein concentration of approximately 2 mg/ml. The membrane preparation was quickly frozen in a bath solution of dry ice and 2-methylbutane (Sigma Chemical Co., St. Louis, Mo.), then stored at −80° C. for no more than 2 weeks. Prior to performing a binding assay an aliquot of frozen membrane was rapidly thawed and protein values determined by the method of Bradford (1976).

Binding was initiated by the addition of 150 μg of $P_2$ membrane to test tubes containing 1 nM of [$^3$H] CP 55,940 (79 Ci/mmol) and a sufficient quantity of buffer to bring the total incubation volume to 1 ml. Nonspecific binding was determined by the addition of 1 μM unlabeled CP 55,940. Following incubation at 30° C. for 1 hr, binding was terminated by addition of ice cold buffer and vacuum filtration through pretreated filters in a 12-well sampling manifold (Millipore, Bedford, Mass.). After washing, filters were placed into plastic scintillation vials (Packard, Downer Grove, Ill.) and shaken. The quantity of radioactivity present was determined by liquid scintillation spectrometry.

$CB_2$ Binding Procedure

Membranes for $CB_2$ binding were obtained from CHO cells. The transfected cell line was maintained in Dublecco's Modified Eagle Medium (Gibco BRL, Grand Island, N.Y.) with 10% fetal clone II (HyClone Laboratories, Inc., Logan, Utah) plus 0.3 to 0.5 mg/ml G418 (to maintain selective pressure) under 5% $CO_2$ at 37% C. Cells were harvested with 1 mM EDTA in phosphate-buffered saline and were centrifuged at 1000×g for 5 min at 4% C. The supernatant was saved and the P1 pellet was resuspended in centrifugation buffer. Homogenization and centrifugation were repeated twice and the combined supernatant fractions were centrifuged at 40,000×g for 30 min at 4% C. The P2 pellet was resuspended in centrifugation buffer 2 (Tris HCl, 50 mM; EDTA, 1 mM; and $MgCl_2$, 3 mM, pH 7.4) to a protein concentration of approximately 2 mg/ml. Protein concentrations were determined by the method of Bradford (1976) using Bio-Rad Protein Assay (Bio-Rad, Richmond, Calif.) and BSA standards (fatty acid free, Sigma Chemical Co., St. Louis, Mo.). The membrane preparation was divided into amounts convenient for binding assays and frozen rapidly in dry ice and stored at −80% C.

Binding was initiated by the addition of 50 μg of quickly thawed P2 membranes to test tubes containing [$^3$H]CP-55,940 (final reaction concentration 0.5 nM), an appropriate concentration of unlabeled CP-55,940 or test drug, and sufficient quantity of assay buffer (50 mM Tris-HCl, 1 mM EDTA, 3 mM $MgCl_2$, 5 mg/ml bovine serum albumin, pH 7.4) to bring the total incubation volume to 0.5 ml. Concentration of [$^3$H]CP-55,940 in saturation studies ranged from 50 to 10,000 pM. Nonspecific binding was determined by the addition of 1 μM unlabeled CP-55,940. CP-55,940 and all cannabinoid analogs were prepared by suspension in assay buffer from a 1 mg/ml ethanolic stock without evaporation of the ethanol (final concentration of no more than 0.4%). In competition studies, analog concentrations ranged from 0.1 nM to 10 μM. After incubation at 30% C for 1 hr, binding was terminated by the addition of 2 ml of ice-cold wash buffer (50 mM Tris-HCl and 1 mg/ml BSA) and vacuum filtration through pre-treated filters in a 12-well sampling manifold (Millipore, Bedford, Mass.). Reaction vessels were washed once with 2 ml of ice-cold wash buffer. Filters were placed into 7-ml plastic scintillation vials (RPI Corp., Mount Prospect, Ill.) with 4 ml of Budget-Solve (RPI Corp.). After shaking for 30 min, the radioactivity present was determined by liquid scintillation spectrometry. Three reaction vessels were used for each drug concentration in each assay. The results represent the combined data of three independent experiments. All assays were performed in siliconized test tubes, which were prepared by air drying (12 hr) inverted borosilicate tubes after two rinses with a 0.1% solution of AquaSil (Pierce, Rockford, Ill.). The GF/C glass-fiber filters (2.4 cm, Baxter, McGaw Park, Ill.) were pre-treated in a 0.1% solution of pH 7.4 polyethylenimine (Sigma Chemical Co.) for at least 6 hr.

Data Analysis

Based on data obtained from numerous previous studies with cannabinoids, maximal cannabinoid effects in each procedure were estimated as follows: 90% inhibition of spontaneous activity, 100% MPE in the tail flick procedure, and −6° C. change in rectal temperature. $ED_{50}$'s were defined as the dose at which half maximal effect occurred. For drugs that produced one or more cannabinoid effect, $ED_{50}$'s were calculated separately using least-squares linear regression on the linear part of the dose-effect curve for each measure in the mouse tetrad, plotted against $\log_{10}$ transformation of the dose. For the purposes of potency comparison, potencies were expressed as μmol/kg.

Pearson product-moment correlation coefficients (with associated significance tests) were calculated between $CB_1$ binding affinity (expressed as log $K_i$) and in vivo potency for each measure (expressed as log $ED_{50}$ in μmol/kg) for all active cannabinoid compounds that bound to the $CB_1$ receptor. In addition, multiple linear regression was used to calculate the overall degree of relationship between $CB_1$ binding affinity and potency in the mouse measures for all active cannabinoids. A correlation between $CB_1$ and $CB_2$ binding affinities was calculated for all compounds that had measurable $K_i$'s for $CB_1$ and $CB_2$ binding ($K_i$<10,000 nM). Ki values for $CB_1$ and $CB_2$ binding were obtained from Scatchard displacement analysis as determined via EBDA program of the KELL software package (Biosoft, Milltown, N.J.).

The $CB_1$ and $CB_2$ binding affinities for substituted biphenyl analogs are shown in Table 1. These compounds contain a phenolic hydroxyl and a lipophilic side chain in the same orientation as in cannabinol. In addition, the pyran oxygen is absent and the analogs have substituents in the phenyl ring (ring C) of cannabinol. Two of the analogs (O-1376 and O-1601) have a dimethylheptyl side chain; each possessed good $CB_1$ and $CB_2$ binding affinities and in vivo activity. O-1601, the more potent of the two active compounds, had a hydroxymethyl group in the phenyl ring. This substitution increased $CB_1$ affinity and in vivo potencies compared to O-1376, but did not affect affinity for $CB_2$ receptors. A similar effect is observed in the cannabinol series where the substitution of a hydroxymethyl group for a methyl at C-9 in cannabinol increased binding affinity and potency (Mahadevan et al., 2000) Shortening the side chain of O-1376 to dimethylbutyl (O-1532) severely decreased affinity for both receptors and resulted in loss of in vivo activity.

Table 2 presents binding and in vivo data for a series of 2-cyclic ring substituted-5-dimethylheptyl resorcinols. Manipulation of the size of the cyclic structure attached at position 2 of the resorcinol ring resulted in changes in binding affinities and potencies. Substitution of a cyclopentane ring (O-1424) resulted in moderate affinity for the $CB_1$ receptor with excellent affinity for the $CB_2$ receptor. Although this compound was active in all three in vivo assays, potency was relatively poor. In addition, potencies across the measures were not equal; i.e., potency for reducing spontaneous activity was approximately half that for producing antinociceptive and hypothermic effects. Increasing ring size to a cyclohexane (O-1422), cycloheptane (O-1656), or adamantyl (O-1660) improved affinity 5- to 14-fold for both cannabinoid receptors and greatly increased potencies in vivo. Substitution of a sulfur for a carbon in a cyclohexane ring (O-1425) decreased $CB_1$ affinity by 14-fold and $CB_2$ affinity by 8-fold (compared to O-1422) as well as reducing in vivo potencies. Similarly, sulfur substitution in a cyclopentane ring (O-1661) also attenuated binding to both cannabinoid receptors. When a methylated nitrogen (O-1662) was inserted into the cyclohexane ring in the same position as the sulfur of O-1425, binding to $CB_1$ receptors did not occur. In addition, $CB_2$ binding was drastically decreased and the compound was not fully active in vivo. In contrast, placing a double bond in the cyclohexane ring (O-1423) decreased affinities and potencies, but the compound remained active. However, moving the lipophilic side chain of O-1422 from C-5 to C4 and replacing the DMH with a n-hexyl chain (O-2010) produced a 865-fold decrease in $CB_1$ affinity and a loss of activity in vivo.

Table 3 shows results of tests with cyclohexane substituted resorcinols in which the position of the substituent at the cyclohexane ring attached to the core resorcinol was varied. All compounds were diastereomeric mixtures. All of these analogs had good ($K_i$=2 nM) to moderate ($K_i$=144 nM) affinity for $CB_1$ receptors and were $CB_2$-selective ($K_i$ range=0.3–13 nM). Methylation at the 2 position of the cyclohexane ring (O-1658) did not dramatically alter affinity for either cannabinoid receptor or in vivo potencies compared to the corresponding cannabinoid with a non-methylated cyclohexane (O-1422 in Table 2). Moving the methyl to position 4 of the cyclohexane ring (O-1659) decreased affinity for both cannabinoid receptors by about 5-fold and produced an even greater decrease (11- to 24-fold) in potencies in vivo. Substituting a phenyl group for the methyl at this same position (O-1663) resulted in 2- to 3-fold decreases in $CB_2$ and $CB_1$ affinities, respectively, and a loss of activity in vivo. In the next five analogs shown in Table 3, the methyl was attached at position 3 of the cyclohexane ring. O-1657 exhibited $CB_1$ and $CB_2$ affinities that were similar to those of O-1658; however, the profiles of in vivo potencies differed. Whereas the two analogs showed approximately equal potencies in suppressing spontaneous activity, O-1658 was twice as potent in producing antinociception and three times as potent in reducing body temperature. By careful chromatography, compound O-1657 was separated into two distinct entities which were designated O-1797-A and O-1798-B. These analogs were still mixtures Affinities of O-1797-A and O-1798-B were 2-3 times greater than those of O-1657. While potencies of these isomers for suppression of locomotor activity and hypothermia were not notably different from those of O-1657, antinociceptive potencies were reduced by about half. The 3R isomer of this series (O-1826) showed decreased affinity for $CB_1$ receptors compared to O-1657; however, affinity for $CB_2$ receptors was identical for both compounds. Not surprisingly, given its decreased $CB_1$ affinity, O-1826 was less potent than O-1657 in vivo. Substitution of a dimethylbutyl for the DMH side chain at C5 of the resorcinol component (O-1890) decreased affinities for both cannabinoid receptors. This compound was active in vivo, although potency was notably low for all measures In contrast, addition of a gem-dimethyl group at the 3 position of the cyclohexane ring with retention of the DMH side chain of the resorcinol component (O-1871) resulted in the best $CB_1$ and $CB_2$ affinities of this series. In vivo potencies, however, were lower than expected for this compound, given its higher $CB_1$ binding affinity.

In order to develop $CB_2$ selective ligands, we examined cyclic ring substituted dimethoxy resorcinols. The $CB_1$ and $CB_2$ binding affinities of these analogs are shown in Tables 4 and 5. Although most of the compounds shown in Tables 4 and 5 possessed a dimethylheptyl side chain, all had poor $CB_1$ affinity; hence, they were not tested in vivo. The bicyclic structure of O-1999 (Table 4) was almost identical to that of O-1657 (Table 3), an analog with good $CB_1$ and $CB_2$ affinities and potent in vivo effects. Both compounds had a dimethylheptyl side chain attached to the 5 position of a resorcinol core that was attached at position 2 to a cyclohexane ring. Each compound had a methyl group at the 3 position of the cyclohexane ring. The major structural difference between the two compounds was that O-1999 was a dimethoxy derivative of the resorcinol O-1657. This seemingly minor structural change from a phenol to a methoxy derivative resulted in complete loss of affinity for $CB_1$ receptors and an almost 600-fold reduction in affinity for $CB_2$ receptors. Similarly, the other analogs that were dimethoxy derivatives of the corresponding resorcinols had poor affinity for $CB_1$ receptors ($K_i$ ranged from 1716 to >10,000), regardless of the cyclic ring substitution at position 2. In contrast, $CB_2$ binding affinities for some of these analogs remained high, as described in more detail below.

Table 4 presents binding data for 2-cyclic ring substituted dimethoxy-resorcinol-DMH analogs that contain at least one oxygen inserted into or attached to the non-resorcinol cyclohexane ring. Compared to O-1999 which did not contain an oxygen in the cyclohexane ring, conversion of the cyclohexane ring to a pyran ring (O-1964) decreased $CB_2$ affinity almost 2-fold without effect on $CB_1$ binding. Further addition of a double bond at position 3 of the pyran ring resulted in O-1965 which did not bind to either cannabinoid receptor. In contrast, the introduction of a tertiary hydroxyl group at C4 of the pyran ring (O-1962) increased $CB_2$ affinity by 3-fold Adding additional oxygens such as a ketol group attached at C-4 to the point of attachment of the dimethoxy resorcinol substituent (O-2092) also increased $CB_2$ affinity whereas adding an oxygen as an epoxide (O-2122) decreased it. The presence of a ketone group at C-4 of the cyclohexane ring and having unsaturation in the ring (O-2114) resulted in a compound with poor affinity for either cannabinoid receptor; however, if a tertiary hydroxyl group was added at the site of dimethoxy resorcinol attachment (O-2115), $CB_2$ affinity improved. Retention of the tertiary hydroxyl, methylation at position 5 and the presence of a ketone at position 3 of the cyclohexane ring increased affinity for both receptors and resulted in a compound (O-2123) with the best affinity ($K_i$=125 nM) in this series.

Table 5 shows $CB_1$ and $CB_2$ affinities for 2-cyclic ring substituted dimethoxy-resorcinol-DMH analogs in which the ring size and the position of the methyl or hydroxyl substituent on the cyclohexane ring are varied. The first analog (O-2072) contains one hydroxyl attached to the cyclohexane at the same position at which the resorcinol core is attached. This compound is $CB_2$-selective. While it had poor affinity for $CB_1$ receptors, it bound with moderate affinity to $CB_2$ receptors. Introduction of a methyl substituent in the 3 position of the cyclohexane ring gave a diastereomeric mixture from which two distinct entities were separated by careful chromatography, These analogs (O-1966-A and O-1967-B) were still mixtures. This substitution resulted in a 5-fold increase in affinity for $CB_2$ receptors with continued poor affinity for $CB_1$ receptors. However, one of these isomers (O-1966-A) showed the best $CB_2$ selectivity (225-fold) in the series and had high binding affinity for the $CB_2$ receptor ($K_i$=22.5 nM). Addition of an extra hydroxyl group to the cyclohexane ring (O-2121) reduced both selectivity and binding affinity for the $CB_2$ receptor comparable to those obtained with O-1967-B. Removal of the methyl at position 3 and addition of an hydroxyl at position 4 resulted in two diastereomeric mixtures which could be separated that were designated as O-2116-A and O-2117-B. Both of these isomers had poor affinity for $CB_1$ receptors, but while the B isomer also had poor affinity for $CB_2$ receptors, the A isomer bound to $CB_2$ receptors with moderate affinity Attachment of a gem-dimethyl group to position 3 of O-2072 (i.e., O-2068) did not significantly alter affinities for $CB_1$ or $CB_2$ receptors; however, replacement of the DMH group of O-2068 with a methyl group (O-2139) produced loss of affinity at both receptors. Changing the dimethyoxy groups of the resorcinol by adding diethoxy groups (O-2090) drastically decreased affinities for $CB_1$ and $CB_2$ receptors (compare O-2090 to O-1966-A or O-1967-B). Enlarging the cyclohexane ring in O-2072 to a cycloheptane ring(O-2091) resulted in little change in affinity for $CB_1$ receptors and an almost 2-fold increase in $CB_2$ affinity.

As stated in the introduction, the lack of $CB_1$ binding affinity of cannabidiol compared to other pyran-ring open analogs such as CP 55,940 prompted us to examine the structure-activity relationships of resorcinol derivatives for in vitro and in vivo cannabinoid activity. Our results show that many of the structural changes that affect $CB_1$ receptor recognition and activation in traditional bicyclic and tricyclic cannabinoids similarly alter binding and activity in this resorcinol series. Previous research has shown that the length and branching of a lipophilic substituent is important for $CB_1$ receptor recognition in all of the major cannabinoid agonist classes, including tetrahydrocannabinols (Compton et al., 1993, incorporated herein by reference), bicyclic cannabinoids (Compton et al., 1993), indole-derived cannabinoids (Wiley et al., 1998 incorporated herein by reference), and anandamides (Ryan et al., 1997; Seltzman et al., 1997 both incorporated herein by reference). In the tricyclic and bicyclic series, a 1',1'-dimethylheptyl side chain is optimal (Compton et al., 1993) and is contained in most of the resorcinols presented here. Reducing the length of this substituent to 1',1'-dimethylbutyl (O-1532 and O-1890) or methyl (O-2139) or a hydrogen (O-2010) resulted in a concomitant elimination or decrease in $CB_1$ receptor recognition, as occurs in other cannabinoid series with similar structural manipulations (see references above).

Other structural features affecting $CB_1$ receptor recognition and activation in this resorcinol series are related to the size, saturation, substitution, and methylation of the second, non-resorcinol ring of these bicyclic cannabinoids. In most tricyclic and bicyclic cannabinoids, the ring corresponding to the non-resorcinol ring in the current series is a cyclohexane. Reducing this size to a cyclopentane decreases $CB_1$ affinity and potency whereas increasing it to a cycloheptane has little effect. Substitution of an adamantyl results in better $CB_1$ affinity; however, potency is decreased. Similar modifications of tricyclic and bicyclic cannabinoids have not been reported. The degree of saturation of the cyclohexane ring, however, has been manipulated in several cannabinoid classes. In the resorcinol series, the presence of a cyclohexane ring appeared optimal, although a thorough investigation of this issue was not undertaken. Introduction of a single double bond (O-1423) within the ring decreased $CB_1$ affinity and potency to the same extent as did a reduction in the size of the ring to a cyclopentane. Hence, most structural manipulations were performed upon a bicyclic resorcinol-cyclohexane template. Degree of saturation of, as well as the position of the double bond in the cyclohexane ring of tricyclic and bicyclic cannabinoids and in the polyolefin loop of the anandamides, has also been shown to affect $CB_1$ receptor recognition and activity in these cannabinoid classes. Greatest affinity and potency within the anandamides is achieved with four double bonds, with greater or lesser saturation resulting in a reduction in $CB_1$ binding and/or in vivo activity (Adams et al., 1995; Sheskin et al., 1997; Thomas et al., 1996). Similarly, number and position of double bonds within the cyclohexane ring of tetrahydrocannabinols and bicyclic cannabinoids affect activity. For example, moving the double bond of $\Delta^9$-THC to position 8 (as in $\Delta^8$-THC) decreases $CB_1$ affinity three-fold and somewhat reduces potency (Compton et al., 1993). Unsaturation of the cyclohexane ring results in cannabinol with its greatly reduced $CB_1$ affinity (Showalter et al., 1996). In contrast, CP 55,940, with a completely saturated cyclohexane ring, is several fold more potent than $\Delta^8$-THC-DMH which has a single double bond in the cyclohexane ring, but $\Delta^8$-THC with its single double bond binds with better $CB_1$ affinity than does $\Delta^{9(11)}$-THC which has a completely saturated cyclohexane ring (Compton et al., 1993).

The most remarkable structural features of the resorcinol series affecting $CB_1$ affinity, however, are the length of the lipophilic side chain at position 5 and the size of the cyclic ring substituent at position 2 of the resorcinol core. THC and CP 55,940 contain two oxygens: one as a phenol (one hydroxyl in the aromatic ring) with a second oxygen incorporated into a separate ring (pyran oxygen in THC) or a hydroxyl group attached as a substituent in the cyclohexane ring as in CP 55,940. Previous research has shown that eliminating the phenolic hydroxyl of $\Delta^8$-THC-like cannabinoids results in deoxy-THC analogs that are $CB_2$-selective (Huffman et al., 1999). Although some of these deoxy-THC analogs also retain reasonable affinity for $CB_1$ receptors, orientation of their binding to $CB_1$ receptors may be inverted such that the pyran oxygen substitutes for the absent phenolic hydroxyl in hydrogen bonding (Huffman et al., 1996). In the absence of a pyran oxygen, as in the resorcinols, the nature of the substituent at position 2 of the resorcinol core is important to maintain adequate $CB_1$ affinity for in vivo activity An acyclic ring was found to be better than a heterocyclic ring with a cyclohexane ring being optimal for in vivo activity. In addition, the size and the position of the substituent on the cyclic ring is important to maintenance of $CB_1$ affinity. The presence of a methyl substituent at position 3 enhanced activity in some cases. Further, the 3R analog (O-1826; Table 2) has a poorer $CB_1$ binding affinity ($K_i$=40 nM) compared to the diastereomeric mixture O-1657 ($K_i$=14 nM, Table 2), suggesting that $CB_1$ binding affinity is enhanced when the orientation of the methyl substituent at position 3 in the cyclohexane ring is 3S compared to 3R. Methylation of the phenols of the resorcinols drastically decreased or eliminated $CB_1$ affinity, perhaps because hydrogen donation is less likely from a methoxy group than from THC's free hydroxyl group (B. R. Martin, unpublished observations). Similarly, methoxy substitution for the phenolic hydroxyl in the methyl esters of $\Delta^8$- and $\Delta^{9(11)}$-THC-DMH resulted in analogs that were $CB_2$-selective and had little affinity for $CB_1$ receptors (Gareau et al., 1996; Huffman et al., 1999; Ross et al., 1999).

Notably, with the exception of a few compounds, the dimethoxyresorcinols tested here were $CB_2$-selective. Most of the structural features that affected recognition at $CB_1$ receptors also affected $CB_2$ receptor recognition, although not always to the same degree or in the same manner. These factors included length and branching of the side chain and size and degree of saturation of the non-resorcinol cyclohexane ring. In a SAR study on a series of $CB_2$-selective deoxy-$\Delta^8$-THC analogs, Huffman et al. (1999) reported that length and branching of the C3 side chain affected $CB_2$ binding in a manner similar to its effect on $CB_1$ affinity, as it did in the present study; however, the range of chain lengths for which moderate to good $CB_2$ affinity was retained for the deoxy-$\Delta^8$-THC analogs was greater than the range for $CB_1$ affinity. Similar results were obtained with a series of $CB_2$-selective indole-derived cannabinoids in which length of the nitrogen substituent was varied (Aung et al., 2000). To date, anandamide analogs appear to be $CB_1$-selective with relatively little affinity for $CB_2$ receptors across several types of manipulations (Showalter et al., 1996). Insufficient research is available to determine the effect of substitution on a cyclohexane ring on $CB_2$ affinity across cannabinoid classes.

Other structural manipulations eliminated or drastically reduced $CB_1$ receptor recognition, but did not necessarily alter $CB_2$ receptor binding in an identical manner. As mentioned, $CB_2$ selectivity was most evident in the dimethoxy analogs, primarily as a consequence of severe reductions in $CB_1$ affinity. HU-308, the most selective $CB_2$ agonist to date, has a dimethoxy resorcinol core structure and does not bind to $CB_1$ receptors at all (Hanu et al., 1999). In addition, greater tolerance in $CB_2$ (vs. $CB_1$) receptor recognition was observed with other C2 substitutions in the resorcinols. Huffman et al. (2001) recently reported that bicyclic pyridone analogs with carbonyl substitution at C1 and a nitrogen substituent substitution at C2 of THC had little affinity for $CB_1$ receptors. In contrast, moderate $CB_2$ affinity (Ki—53 nM) was retained. Differences in allosteric regulation of $CB_1$ and $CB_2$ receptors by ions and guanine nucleotides has been noted previously (Showalter et al., 1996). Together, results presented here and elsewhere (see above) suggest incomplete overlap of the pharmacophores for $CB_1$ and $CB_2$ receptors.

In summary, structure-activity relationships of the resorcinol series presented here are consistent with the $CB_1$ and $CB_2$ pharmacophores of other cannabinoid classes, including tetrahydrocannabinols, bicyclic cannabinoids, aminoalkylindoles, and anandamides. In this series of resorcinols, several structural features were essential for maintenance of $CB_1$ receptor recognition and in vivo activity, including the presence of a branched lipophilic side chain (DMH) at C5, the presence of free phenols, and substitution of a cyclohexane ring at C2. An important structural feature for receptor recognition at $CB_2$ receptors was side chain length, as reduction of the chain length to a methyl eliminated $CB_2$ binding affinity. The $CB_2$ selectivity observed with some resorcinols was maximized in the dimethoxyresorcinol analogs and this selectivity was greatly enhanced when a tertiary hydroxyl group was present in the cyclohexane ring in the same position at which the resorcinol core is attached. In contrast, the presence of unsaturation or a ketone group or an additional hydroxyl substitution in the cyclohexane ring adversely affected the $CB_2$ selectivity. Methyl ethers were optimal for $CB_2$ selectivity since ethyl ethers reduced selectivity.

In conclusion, although resorcinol derivatives with cyclic ring substituents at C2 are closely related to the nonactive cannabinoid cannabidiol, many of these analogs have high $CB_1$ and/or $CB_2$ binding affinity as well as potent in vivo activity. In addition, because dimethoxyresorcinols are $CB_2$ selective, they have potential to offer insight into similarities and differences between requirements for receptor recognition at $CB_1$ versus $CB_2$ receptors. One such difference noted here was the greater tolerance found for substitution at position 2, in the resorcinol series, for $CB_2$ receptor recognition compared to that for $CB_1$ receptors. The results presented here suggest that the resorcinol series represent a novel template for the development of $CB_1$ and $CB_2$ selective cannabinoid agonists.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

REFERENCES—INCORPORATED HEREIN BY REFERENCE

Adams I B, Ryan W, Singer M, Thomas B F, Compton D R, Razdan R K, Martin B R (1995) Evaluation of cannabinoid receptor binding and in vivo activities for anandamide analogs. *J Pharmacol Exp Ther* 273: 1172–1181.

Aung M M, Griffin G, Huffman J W, Wu M J, Keel C, Yang B, Showalter V M, Abood M E, Martin B R (2000) Influence of the N-1 alkyl chain length of cannabimimetic indoles upon $CB_1$ and $CB_2$ receptor binding. *Drug Alcohol Depend* 60: 133–140.

Bradford M M (1976) A rapid and sensitive method for the quantitation of microgram quantities of protein utilizing the principle of protein-dye binding. *Anal Biochem* 72: 248–254.

Compton D R, Rice K C, De Costa B R, Razdan R K, Melvin L S, Johnson M R, Martin B R (1993) Cannabinoid structure-activity relationships: Correlation of receptor binding and in vivo activities. *J Pharmacol Exp Ther* 265: 218–226.

Crocker P J, Saha B, Ryan W J, Wiley J L, Martin B R, Ross R A, Pertwee R G, Razdan R K (1999) Development of agonists, partial agonists and antagonists in the tetrahydrocannabinol series. *Tetrahedron* 55: 13907–13926.

D'Ambra T E, Estep K G, Bell M R, Eissenstat M A, Josef K A, Ward S I, Haycock D A, Baizman E R, Casiano F M, Beglin N C, Chippazi S M, Grego I D, Kullnig R K, Daley G T (1992) Conformationally restrained analogues of pravadoline: Nanomolar potent, enantioselective (aminoalkyl)indole agonists of the cannabinoid receptor *J Med Chem* 35: 124–135.

Devane W A, Dysarz III F A, Johnson M R, Melvin L S, and Howlett A C (1988) Determination and characterization of a cannabinoid receptor in rat brain. *Mol Pharmacol* 34:605–613.

Gareau Y, Dufresne C, Gallant M, Rochette C, Sawyer N, Slipetz D M, Tremblay N, Weech P K, Metters K M, Labelle M (1996) Structure activity relationships of tetrahydrocannabinol analogues on human cannabinoid receptors. *BioOrg Med Chem* 6: 189–194.

Hanu L, Breuer A, Tchilibon S, Shiloah S, Goldenberg D, Horowitz M, Pertwee R G, Ross R A, Mechoulam R (1999) HU-308: A specific agonist for CB2, a peripheral cannabinoid receptor. *Proc Nat Acad Sci USA* 96: 14228–14233.

Huffman J W, Lu J, Hynd G, Wiley J L, Martin B R (2001) A pyridone analogue of traditional cannabinoids. A new class of selective ligands for the $CB_2$ receptor. *BioOrg Med Chem*, in press.

Huffman J W, Liddle J, Yu S, Aung M M, Abood M E, Wiley J L, Martin B R (1999) 3-(1',1'-Dimethylbutyl)-1-deoxy-$^8$-THC and related compounds, Synthesis of selective ligands for the $CB_2$ receptor. *BioOrg Med Chem* 7: 2905–2914.

Huffman J W, Yu S, Showalter V, Abood M E, Wiley J L, Compton D R, Martin B R, Bramblett R D, Reggio P H (1996) Synthesis and pharmacology of a very potent cannabinoid lacking a phenolic hydroxyl with high affinity for the CB2 receptor *J Med Chem* 39: 3875–3877.

Little P J, Compton D R, Johnson M R, Melvin L S, Martin B R (1988) Pharmacology and stereoselectivity of structurally novel cannabinoids in mice. *J Pharmacol Exp Ther* 247: 1046–1051.

Mahadevan A, Siegal C, Martin B R, Abood M E, Beletskaya I, Razdan R K (2000) Novel cannabinol probes for CB1 and CB2 cannabinoid receptors. *J Med Chem* 43: 3778–3785.

Munro S, Thomas K L, Abu-Shaar M (1993) Molecular characterization of a peripheral receptor for cannabinoids. *Nature* 365: 61–65.

Reggio P H, Wang T, Brown A E, Fleming D N, Seltzman H H, Griffin G, Pertwee R G, Compton D R, Abood M E, Martin B R (1997) Importance of the C-1 substituent in classical cannabinoids to $CB_2$ receptor selectivity, Synthesis and characterization of a series of O,2-propano-$^8$-tetrahydrocannabinol analogs. *J Med Chem* 40: 3312–3318.

Rinaldi-Carmona M, Barth F, Heaulme M, Shire D, Calandra B, Congy C, Martinez S, Maruani J, Neliat G, Caput D, Ferrara P, Soubrie P, Breliere J C, Le Fur G (1994) S R 141716A, a potent and selective antagonist of the brain cannabinoid receptor. *FEBS Lett* 350: 240–244.

Ross R A, Brockie H C, Stevenson L A, Murphy V L, Templeton F, Makriyannis A, Pertwee R G (1999) Agonist-inverse agonist characterization at $CB_1$ and $CB_2$ cannabinoid receptors of L759633, L759656 and AM630. *Br J Pharmacol* 126: 665–672.

Ryan W J, Banner W K, Wiley J L, Martin B R, Razdan R K (1997) Potent anandamide analogs: The effect of changing the length and branching of the end pentyl chain. *J Med Chem* 40: 3617–3625.

Seltzman H H, Fleming D N, Thomas B F, Gilliam A F, McCallion D S, Pertwee R G, Compton D R, Martin B R (1997) Synthesis and pharmacological comparison of dimethylheptyl and pentyl anandamide analogs. *J Med Chem* 40: 3626–3634.

Sheskin T, Hanu L, Slager J, Vogel Z, Mechoulam R (1997) Structural requirements for binding of anandamide-type compounds to the brain cannabinoid receptor. *J Med Chem* 40: 659–667.

Sheskin T, Hanu L, Slager J, Vogel Z, Mechoulam R (1997) Structural requirements for binding of anandamide-type compounds to the brain cannabinoid receptor. *J Med Chem* 40: 659–667.

Showalter V M, Compton D R, Martin B R, Abood M E (1996) Evaluation of binding in a transfected cell line expressing a peripheral cannabinoid receptor (CB2): identification of cannabinoid receptor subtype selective ligands. *J Pharmacol Exp Ther* 278: 989–999.

Song Z H, Bonner T I (1996) A lysine residue of the cannabinoid receptor is critical for receptor recognition by several agonists but not WIN-55,212. *Mol Pharmacol* 49, 891–896.

Thomas B F, Adams I B, Mascarella W, Martin B R, Razdan R K (1996) Structure-activity analysis of anandamide analogs: Relationship to a cannabinoid pharmacophore. *J Med Chem* 39: 471–479.

Wiley J L, Compton D R, Dai D, Lainton J A H, Phillips M, Huffman J W, Martin B R (1998) Structure-activity relationships of indole- and pyrrole-derived cannabinoids. *J Pharmacol Exp Ther* 285: 995–1004.

The disclosures of all of the above-cited references are incorporated herein by reference.

TABLE 1

CB$_1$ and CB$_2$ Binding Affinities and Pharmacological Effects of Phenols

|  | ID | R | R1 | K$_i$ (nM) CB$_1$ | CB$_2$ | CB$_1$/CB$_2$ | ED$_{50}$ SA | TF | RT |
|---|---|---|---|---|---|---|---|---|---|
| 1 | O-1376 | CH$_3$ | DMH | 33 ± 4 | 3 ± 0.4 | 11 | 8.5 (5–16) | 5.7 (3–10) | 2.3 (1–5) |
| 2 | O-1532 | CH$_3$ | DM-butyl | 876 ± 18 | 113 ± 21 | 8 | 32% (30) | 7% (30) | −0.4 (30) |
| 3 | O-1601 | CH$_2$OH | DMH | 5 ± 0.6 | 3 ± 0.4 | 2 | 1.1 (0.8–1.4) | 1.1 (0.8–1.4) | 1.6 (1.4–2.2) |

The K$_i$'s are presented as means ±SEM. All ED$_{50}$'s are expressed as μmol/kg (with 95% confidence limits in parentheses). For compounds that failed to produce either manual or dose-related effects, the percent effect at the highest dose (mg/kg: in parenthesis) is provided. SA=suppression of spontaneous activity; MPE=% maximum possible antinociceptive effect in tail flick assay; RT=rectal temperature. DMH=dimethylheptyl.

TABLE 2

Pharmacological Effects and Cannabinoid Receptor Binding Affinities of Bicyclic Resorcinols

| ID | R | R1 | R2 | K$_i$ (nM) CB$_1$ | CB$_2$ | CB$_1$/CB$_2$ | ED$_{50}$ SA | TF | RT |
|---|---|---|---|---|---|---|---|---|---|
| O-1424 | cyclopentyl | DMH | H | 95 ± 6 | 7 ± 0.4 | 14 | 27 (13–56) | 13 (9–23) | 13 (10–20) |
| O-1422 | cyclohexyl | DMH | H | 11 ± 2 | 1.5 ± 0.1 | 7 | 0.1 (0.02–0.6) | 0.6 (0.5–1.1) | 0.6 (0.5–0.7) |
| O-1656 | cycloheptyl | DMH | H | 18 ± 1 | 2 ± 0.2 | 9 | 1.5 (0.4–7.0) | 1.2 (0.9–1.5) | 0.6 (0.1–8.7) |
| O-1660 | adamantyl | DMH | H | 7 ± 1 | 3 ± 0.8 | 2 | 3.5 (3.2–3.8) | 2.4 (1.9–3.0) | 4.6 (2.4–9.2) |

TABLE 2-continued

Pharmacological Effects and Cannabinoid Receptor Binding Affinities of Bicyclic Resorcinols

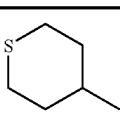

| ID | R | R1 | R2 | $K_i$ (nM) CB$_1$ | $K_i$ (nM) CB$_2$ | CB$_1$/CB$_2$ | ED$_{50}$ SA | ED$_{50}$ TF | ED$_{50}$ RT |
|---|---|---|---|---|---|---|---|---|---|
| O-1425 | 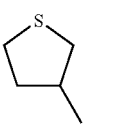 | DMH | H | 153 ± 17 | 12 ± 2 | 13 | 17 (10–29) | 15 (10–24) | 13 (10–19) |
| O-1661 | 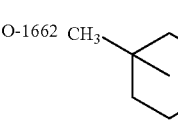 | DMH | H | 138 ± 4 | 28 ± 12 | 5 | 24 (13–42) | 14 (9–20) | 24 (17–34) |
| O-1662 | 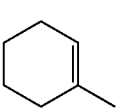 | DMH | H | >10,000 | 5424 ± 1103 | — | 87% (30) | 30% (30) | −3 (30) |
| O-1423 | 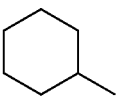 | DMH | H | 97 ± 5 | 28 ± 5 | 3 | 12 (8–20) | 9 (7–13) | 9 (6–15) |
| O-2010 | 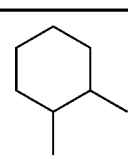 | H | C$_6$H$_{13}$ | 9515 ± 332 | NT | — | −18% (30) | 9% (30) | −0.4 (30) |

The $K_i$'s are presented as means ±SEM. All ED$_{50}$'s are expressed as μmol/kg (with 95% confidence limits in parentheses). For compounds that filed to produce either maximal or dose-related effects, the percent effect at the highest dose (mg/kg: in parenthesis) is provided. SA=suppression of spontaneous activity; MPE=% maximum possible antinociceptive effect in tail flick assay; RT=rectal temperature.

TABLE 3

In Vitro and In Vivo Cannabinoid Effects of Bicyclic Resorcinols with Methylated Cyclohexane

| ID | R | R1 | $K_i$ (nM) CB$_1$ | $K_i$ (nM) CB$_2$ | CB$_1$/CB$_2$ | ED$_{50}$ SA | ED$_{50}$ TF | ED$_{50}$ RT |
|---|---|---|---|---|---|---|---|---|
| O-1658 | | DMH | 16 ± 2 | 1 ± 0.3 | 16 | 0.2 (0.1–0.3) | 0.3 (0.2–0.3) | 0.3 (0.27–0.5) |

TABLE 3-continued

In Vitro and In Vivo Cannabinoid Effects of Bicyclic Resorcinols with Methylated Cyclohexane

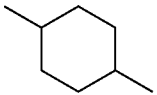

| ID | R | R1 | $K_i$ (nM) CB$_1$ | $K_i$ (nM) CB$_2$ | CB$_1$/CB$_2$ | ED$_{50}$ SA | ED$_{50}$ TF | ED$_{50}$ RT |
|---|---|---|---|---|---|---|---|---|
| O-1659 | 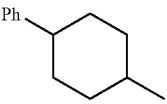 | DMH | 45 ± 1 | 5 ± 0.9 | 9 | 4.8 (3–9) | 3.9 (3–6) | 3.3 (2–5) |
| O-1663 | Ph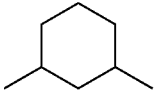 | DMH | 144 ± 22 | 9 ± 2 | 16 | 32% (30) | 7% (30) | −2.2 (30) |
| O-1657 | 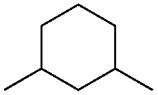 | DMH | 14 ± 0.5 | 0.8 ± 0.04 | 17 | 0.3 (0.3–0.5) | 0.6 (0.5–1) | 0.9 (0.7–1.1) |
| O-1797A | 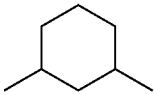 | DMH | 5 ± 0.6 | 0.4 ± 0.03 | 12 | 0.5 (0.4–0.6) | 1.1 (0.8–1.5) | 0.7 (0.6–1.0) |
| O-1798B | 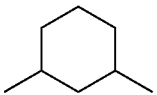 | DMH | 4 ± 0.6 | 0.5 ± 0.07 | 8 | 0.2 (0.03–1.2) | 1.0 (0.7–1.6) | 0.6 (0.5–0.7) |
| O-1826 | 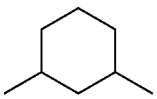 | DMH | 40 ± 11 | 0.8 ± 0.05 | 50 | 2.7 (2.1–3.9) | 2.4 (1.8–3.3) | 3.6 (2.7–4.5) |
| O-1890 | 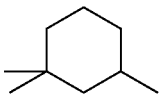 | DM-butyl | 96 ± 4 | 13 ± 1 | 7 | 69 (55–90) | 48 (51–69) | 72 (45–114) |
| O-1871 | 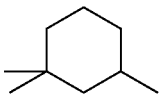 | DMH | 2 ± 0.3 | 0.3 ± 0.01 | 7 | <1.0$^a$ | 2.3 (2.0–2.6) | 1.3 (0.3–4.3) |

$^a$This dose (µmol/kg) produced >50% inhibition and was the lowest dose tested. The K's are presented as means ± SEM. All ED$_{50}$'s are expressed as µmol/kg (with 95% confidence limits in parentheses). For compounds that failed to produce either maximal or dose-related effects the percent effect as the highest dose (mg/kg; in parenthesis) is provided. SA = suppression of spontaneous activity: MPE = % maximum possible antinociceptive effect in tail flick assay; RT = rectal temperature.

TABLE 4

CB₁ and CB₂ Binding Affinities of Dimethoxy-Dimethylheptyl Resorcinol Analogs

| ID | R (CH₂OH) | $K_i$ (nM)* CB$_1$ | $K_i$ (nM)* CB$_2$ | CB$_1$/CB$_2$ |
|---|---|---|---|---|
| 22 | HU-308[a] | >10,000 | 23 ± 4 | — |
| 23 | O-1999 | >10,000 | 466 ± 110 | — |
| 24 | O-1964 | >10,000 | 911 ± 116 | — |
| 25 | O-1965 | >10,000 | >10,000 | — |
| 26 | O-1962 | >10,000 | 342 ± 22 | — |
| 27 | O-2092 | 4581 ± 312 | 126 ± 12 | 36 |
| 28 | O-2122 | 3758 ± 184 | 1065 ± 107 | 4 |
| 29 | O-2114 | 8442 ± 954 | 1773 ± 184 | 5 |
| 30 | O-2115 | 4572 ± 173 | 346 ± 49 | 13 |

TABLE 4-continued

CB$_1$ and CB$_2$ Binding Affinities of Dimethoxy-Dimethylheptyl Resorcinol Analogs

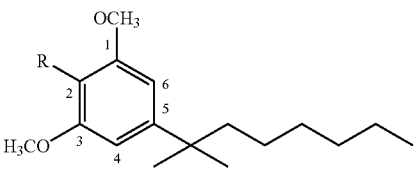

| | | CH$_2$OH | K$_i$ (nM)* | | |
|---|---|---|---|---|---|
| ID | R | | CB$_1$ | CB$_2$ | CB$_1$/CB$_2$ |
| 31 | O-2123 | | 1731 ± 117 | 125 ± 14 | 14 |

*The K$_i$'s are presented as means ± SEM.
[a]Values from Hanu__et al__1999. Note: Binding ligand. [$^3$H]HU-243, was different from that used in present study.

TABLE 5

CB$_1$ and CB$_2$ Binding Affinities of Hydroxylated Dimethoxy-Dimethylheptyl Resorcinols

| | | | | | K$_i$ (nM) | | |
|---|---|---|---|---|---|---|---|
| ID | R | | R1 | R2 | CB$_1$ | CB$_2$ | CB$_1$/CB$_2$ |
| 32 | O-2072 | | OCH$_3$ | DMH | 5820 ± 662 | 105 ± 19 | 55 |
| 33 | O-1966A | | OCH$_3$ | DMH | 5055 ± 984 | 23 ± 2.1 | 220 |
| 34 | O-1967B | | OCH$_3$ | DMH | 1716 ± 105 | 111 ± 8 | 15 |
| 35 | O-2121 | | OCH$_3$ | DMH | 1990 ± 77 | 101 ± 14 | 20 |
| 36 | O-2116A | | OCH$_3$ | DMH | 3932 ± 483 | 190 ± 17 | 21 |

TABLE 5-continued

CB$_1$ and CB$_2$ Binding Affinities of Hydroxylated Dimethoxy-Dimethylheptyl Resorcinols

| ID | | R | R1 | R2 | K$_i$ (nM) CB$_1$ | K$_i$ (nM) CB$_2$ | CB$_1$/CB$_2$ |
|---|---|---|---|---|---|---|---|
| 37 | O-2117B | (hydroxycyclohexyl-methyl with OH) | OCH$_3$ | DMH | >10,000 | 1561 ± 70 | — |
| 38 | O-2068 | (dimethyl-hydroxycyclohexyl) | OCH$_3$ | DMH | 7515 ± 721 | 161 ± 24 | 47 |
| 39 | O-2139 | (dimethyl-hydroxycyclohexyl) | OCH$_3$ | CH$_3$ | >10,000 | >10,000 | — |
| 40 | O-2090 | (dimethyl-hydroxycyclohexyl) | OC$_2$H$_5$ | DMH | 8810 ± 422 | 858 ± 43 | 10 |
| 41 | O-2091 | (hydroxy-methylcycloheptyl) | OCH$_3$ | DMH | 3201 ± 141 | 64 ± 8 | 50 |

The K$_i$'s are presented as means ±SEM.

| A RAZ-DAN O# | C | D STRUCTURE | I CB1 KI (μM) |
|---|---|---|---|
| O-1376 | O-1376 = 3-1',1'-Dimethylheptyl-6-(2-isopropyl-5-methylphenyl)phenol | | 32.7 ± 4.0 |
| O-1422 | O-1442 = Cyclohexyl-5-(1',1'-dimethylheptyl)-resorcinol | | 11.33 ± 2 |

| | | | | |
|---|---|---|---|---|
| 5 | O-1423 | O-1423 = 2-(Cyclohex-1'-enyl)-5-(1',1'-dimethylheptyl-rescorcinol | 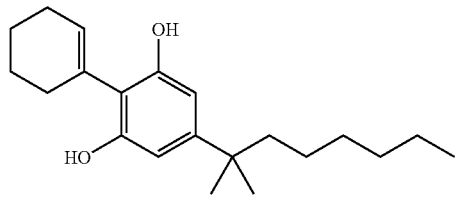 | 96.65 ± 5 |
| 6 | O-1424 | O-1424 = 2-(Cyclopentyl)-dimethylheptyl-resorcinol | 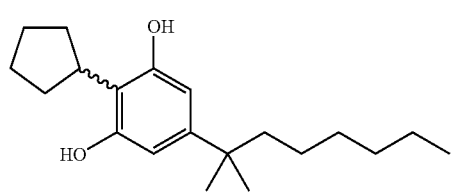 | 94.88 ± 6 |
| 7 | O-1425 | O-1425 = 2-(4'-Tetrahydrothiopyranyl)-5-(1',1'-dimethylheptyl-rescorcinol | 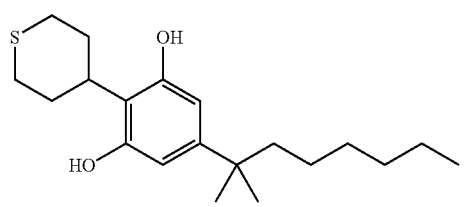 | 152.84 ± 17 |
| 8 | O-1532 | 3-1',1'-Dimethylbutyl-6-(2-isopropyl-5-methyl-phenyl-phenyl | 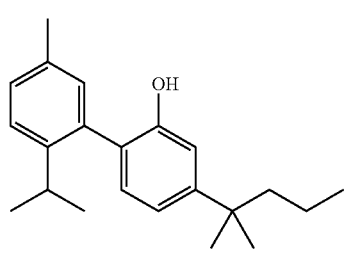 | 876 ± 18.45 |
| 9 | O-1601 | 3-1',1'-Dimethylheptyl-6-(2-isopropyl-5-hydroxy-methylphenyl)-phenol | 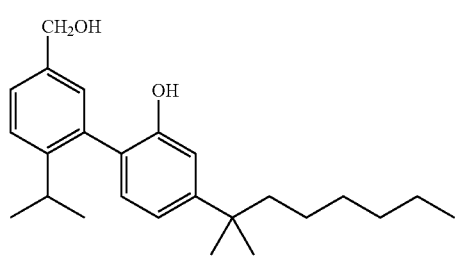 | 4.82 ± 0.56 |
| 10 | O-1602 | (−)-4-(3,3,4-trans-p-Menthadien-(1,8)-yl-orcinol | 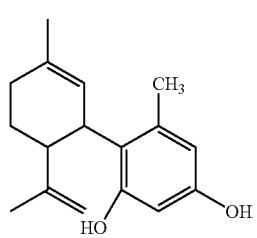 | >10,000 |
| 11 | O-1656 | 2-Cyclohexyl-5-(1',1'-dimethyl-heptyl)-resorcinol | 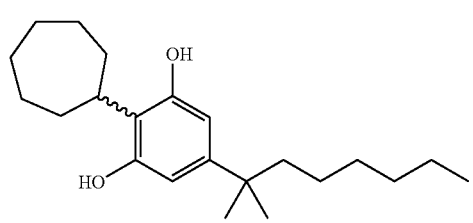 | 17.8 ± 1.4 |

-continued

| | | | | |
|---|---|---|---|---|
| 12 | O-1657 | 2-(3-Methylcyclohexyl)-5-(1',1'-dimethylheptyl)-resorcinol | 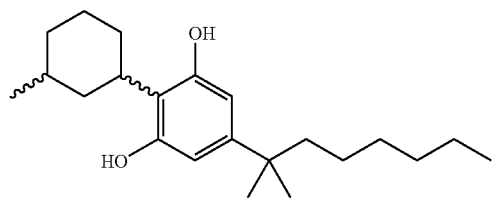 | 14.4 ± 0.53 |
| 13 | O-1658 | 2-(2-Methylcyclohexyl)-5-(1',1'-dimethylheptyl)-resorcinol | 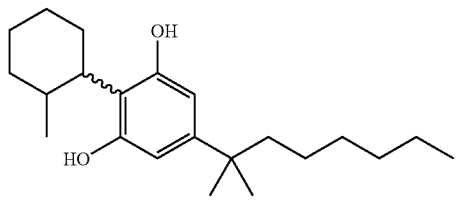 | 16.5 ± 1.7 |
| 14 | O-1659 | 2-(4-Methylcyclohexyl)-5-(1',1'-dimethylheptyl)-resorcinol | 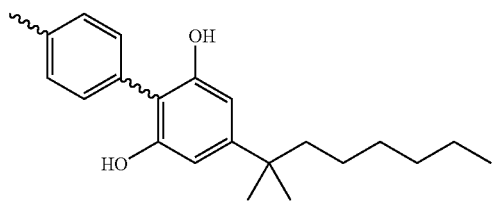 | 45.22 ± 1.52 |
| 15 | O-1660 | 2-(2-Adamantyl)-5-(1',1'-dimethylheptyl)-resorcinol | 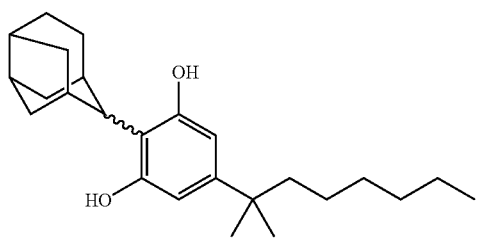 | 7.5 ± 1.2 |
| 16 | O-1661 | 2-(Tetrahydrothiophen-3-yl)-5-(1',1'-dimethylheptyl)-resorcinol | 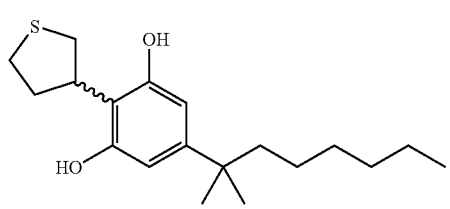 | 138 ± 3.7 |
| 17 | O-1662 | 2-(1-Methylpiperidin-4-yl)-5-(1',1'-dimethylheptyl)-resorcinol | 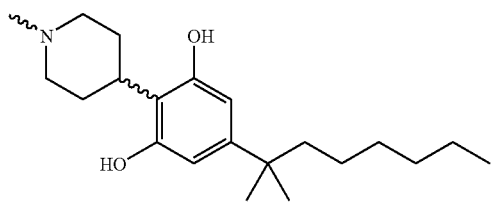 | >10,000 |
| 18 | O-1663 | 2-(4-Phenylcyclohexyl)-5-(1',1'-dimethylheptyl)-resorcinol | 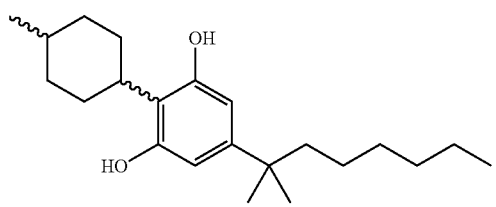 | 143.7 ± 21.9 |

| | | | | |
|---|---|---|---|---|
| 19 | O-1297 | 2-(3-Methylcyclohexyl)-5-(1',1'-dimethylheptyl-resorcinol isomer A | 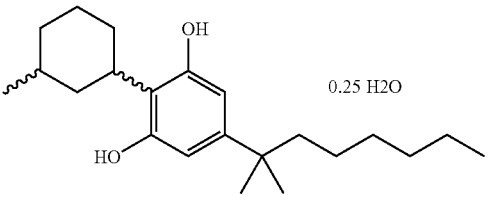 0.25 H2O | 5.21 ± 0.57 |
| 20 | O-1798 | 2-(3-Methylcyclohexyl)-5-(1',1'-dimethylheptyl)-resorcinol isomer B | 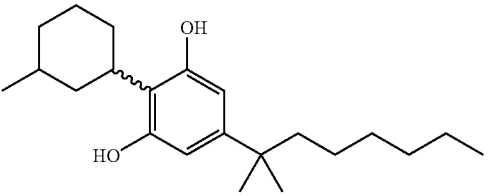 | 4.33 ± 0.58 |
| 21 | O-1871 | (−)-2-(3,3,4-trans-p-menthadien-(1,8)-yl)-orcinol | 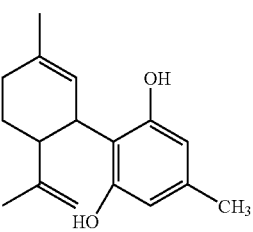 | >10,000 |
| 22 | O-1826 | 2-(3R-Methylcyclohexyl)-5-(1',1'-dimethylheptyl)resorcinol | 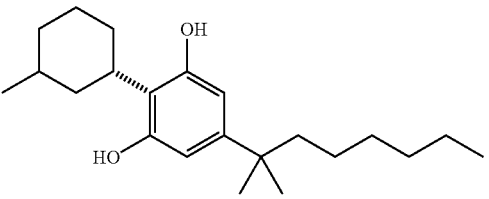 | 40 ± 10.9 |
| 23 | O-1847 | (−)-2-(3,4-trans-p-menthadien(1,8)-yl-resorcinol | 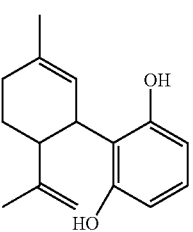 | >10,000 |
| 24 | O-1848 | (−)-4-(3,4-trans-p-menthadien-(1,8)-yl)-resorcinol | 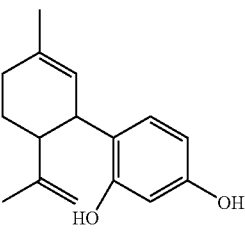 | >10,000 |
| 25 | O-1868 | (−)-2-(3-3,4-trans-p-menthadien(1,8)-yl)-4,6-diododecanol | 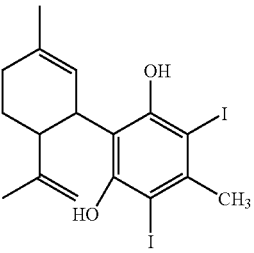 | >10,000 |

| | | | | |
|---|---|---|---|---|
| 26 | O-1871 | 2-(3,3-Dimethylcyclohexyl-5-(1',1'-dimethylheptyl)-resorcinol | 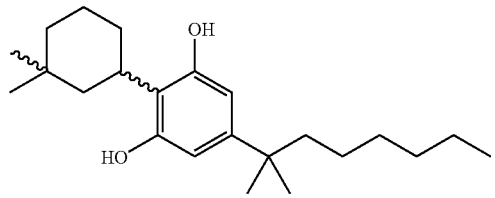 | 2.3 ± 0.32 |
| 27 | O-1890 | 2-(3-Methylcyclohexyl)-5-(1',1'-dimethylbutyl)-resorcinol | 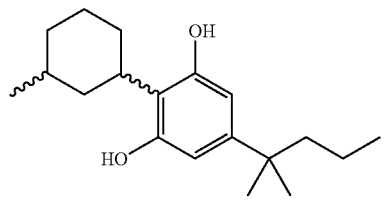 | 96.1 ± 3.53 |
| 28 | O-1917 | 2-Cyclohexyl-5-methyl-resorcinol | 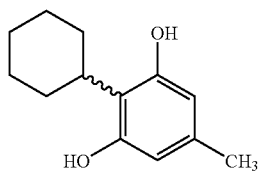 | |
| 29 | O-1918 | (−)-1,3-O-methoxy-2-(3,3,4-trans-p-menthadien-(1,6)-yl)-orcinol | 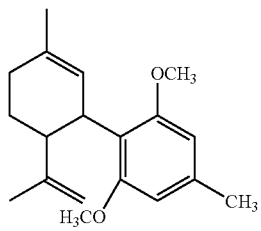 | |
| 30 | O-1919 | (−)-2-(3,3,4-trans-p-menthadien-(1,8)-yl)-monomethoxyorcinol | 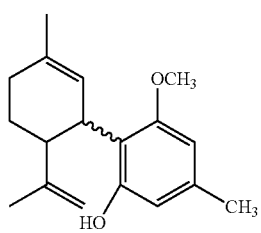 | |
| 31 | O-1962 | O-1962 4-(4-(1,1-Dimethylheptyl)-2,6-dimethoxyphenyl)-tetrahydropyran-4-ol | 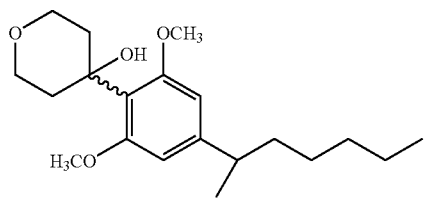 | >10,000 |
| 32 | O-1964 | O-1964 4-(4-(1,1-Dimethylheptyl)-2,6-dimethoxy-phenyl)-tetrahydropyran | 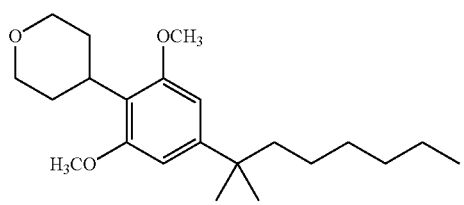 | >10,000 |

| | | | |
|---|---|---|---|
| 33 | O-1965 | O-1965<br>4-(4-(1,1-Dimethylheptyl)-2,6-dimethoxy-phenyl)-3,6-dihydro-2H-pyran | >10,000 |
| 34 | O-1966 | O-1966<br>1-(4-(1,1-Dimethylheptyl-2,6-dimethoxy-phenyl)-3-methyl-cyclohexanol isomer 1 | 5055 ± 983.8 |
| 35 | O-1967 | O-1967<br>1-(4-(1,1-Dimethylheptyl-2,6-dimethoxy-phenyl)-3-methyl-cyclohexaol isomer 2 | 1716.3 ± 104.8 |
| 36 | O-1999 | O-1999<br>5-(1,1-Dimethyl-heptyl-1,3-dimethoxy-2-(3-methylcyclohexyl)benzene | >10,000 |
| 37 | O-2010 | O-2010<br>2-Cyclohexyl-4-hexyl resorcinol | 9515 ± 332.5 |
| 38 | O-2068 | O-2068<br>1-(4-(1,1-Dimethylheptyl)-2,6-dimethoxy phenyl)-3,3-dimethyl-cyclohexanol | 7515 ± 720.9 |
| 39 | O-2072 | O-2072<br>1-(4-(1,1-Dimethylheptyl)-2,5-dimethox phenyl)-cyclohexanol | 5820.33 ± 662.31 |
| 40 | O-2090 | O-2090<br>1-(4-(1,1-Dimethlheptyl)-2,6-diol) phenyl)-3-methylcyclohexane-1-o | 8809.67 ± 422.15 |

| | | | |
|---|---|---|---|
| 41 | O-2091 | O-2091<br>1-(4-(1,1-Dimethylheptyl)-2,6-dime phenyl)-cycloheptan-1-ol | 3200.67 ± 141.04 |
| 42 | O-2092 | O-2092<br>8-(4-(1,1-Dimethylheptyl)-2,6-dim phenyl)-1,4-dioxaspiro(4,5)decan- | 4581.33 ± 311.65 |
| 43 | 2114 | 4-(4-(1,1-O-methyl-heptyl)-2,6-dimethoxy-phenyl)-cyclohex-3-enone | 8441.7 ± 954.3 |
| 44 | 2115 | 4-(4-(1,1-Dimethylheptyl)-2,4-dimethoxy-phenyl-1-hydroxy-cyclohexane | 4571.7 ± 173.4 |
| 45 | 2116 | 1-(4-(1,1-Dimethyl-heptyl)-2,5-dimethoxy-phenyl-cyclohexane-1,6-diol (A) | 3931.7 ± 483.4 |
| 46 | 2117 | 1-(4-(1,1-Dimethyl-heptyl-2,6-dimethoxy-phenyl)-cyclohexane-1,4-diol (B) | >10,000 |
| 47 | 2118 | Name of the stucture not green, also structure needs an arom-assertly its drawn with MW formula C22H30O2, should be C24H32O3 | 6444.3 ± 1389.5 |

-continued

| | | | | |
|---|---|---|---|---|
| 48 | 2121 | 1-(6-(1,1-Dimethylheptyl)-2,6-dimethylphenyl)-5-methyl-cyclohexane-1,3-diol | | 1990 ± 26.66 |
| 49 | 2122 | 5-(4-(1,1-Cycloheptyl-2,6-dimethoxy-phenyl)-7-oxa-bicyclo-(1,0)heptene-3-ol | | 3757.67 ± 184.15 |
| 50 | 2123 | 3-(4-(1,1-Dimethylheptyl)-2,6-dimethoxy-phenyl)-3-hydroxy-5-methylcyclohexane | | 1730.67 ± 116.86 |
| 51 | 2437 | O-2437 1-(4-(1,1-Dimethyl-heptyl)-2,6-dimethoxy-phenyl)-3-methyl-cyclohexanol | | 2665 ± 145.31 |
| 52 | 2139 | O-2139 1-(2,6-Dimethyoxy-methyl-phenyl)-3,3-dimethyl-cyclohexanol | | >10,000 |
| 53 | O-2298 | 1-(2,6-Dimethoxy-4-methyl-pheny)-cyclohexanol | | >10,000 |
| 54 | O-2299 | 2-Cyclohexyl-1,3-dimethoxy-5-methylbenzene | | >10,000 |

| | J CB2KI μM | K S.A | L T.F. | M R.T. | N Publication |
|---|---|---|---|---|---|
| | | | ED50 (mg/kg) or % effect at dose | | |
| 3 | 2.63 ± 0.36 | 2.944 | 1.97 | 0.822 | Wiley et al. (in press) |
| 4 | 1.46 ± 0.1 | 0.3794 | 0.2412 | 0.19394 | Wiley et al. (in press) |

-continued

| | | | | | |
|---|---|---|---|---|---|
| 5 | 27.62 ± 5.13 | 3.918 | 2.856 | 2.944 | Wiley et al. (in press) |
| 6 | 6.66 ± 0.43 | 8.294 | 4.481 | 4.239 | Wiley et al. (in press) |
| 7 | 12.18 × 2.09 | 5.819 | 5.049 | 4.526 | Wiley et al. (in press) |
| 8 | 112.6 ± 21 | | | | Wiley et al. (in press) |
| 9 | 2.91 ± 0.43 | | | | Wiley et al. (in press) |
| 10 | >10,000 | 66% stim. @ 30 | 0 @ 30 | 0.3 @ 30 | |
| 11 | 2.12 ± 0.25 | 0.53 | 0.39 | 0.21 | Wiley et al. (in press) |
| 12 | 0.82 ± 0.04 | 0.13 | 0.23 | 0.29 | Wiley et al. (in press) |
| 13 | 1.38 ± 0.33 | 0.06 | 0.09 | 0.12 | Wiley et al. (in press) |
| 14 | 4.73 ± 0.94 | 1.65 | 1.35 | 1.12 | Wiley et al. (in press) |
| 15 | 3.86 ± 0.81 | 1.273 | 0.911 | 1.729 | Wiley et al. (in press) |
| 16 | 27.7 ± 12.1 | 2.648 | 4.389 | 7.781 | Wiley et al. (in press) |
| 17 | 5424 ± 1103 | 77% stim. @ 10 | 7 @ 10 | 1 @ 10. Lethal @ 30 | Wiley et al. (in press) |
| 18 | 8.8 ± 1.6 | 32% @ 30 | 7% @ 30 | neg 12' @ 30 | Wiley et al. (in press) |
| 19 | 0.44 ± 0.03 | 0.154 | 0.362 | 0.252 | Wiley et al. (in press) |
| 20 | 0.48 ± 0.07 | 0.070 | 0.379 | 0.218 | Wiley et al. (in press) |
| 21 | | 0 @ 30 | 8 @ 30 | neg 1 @ 30 | |
| 22 | 0.8 ± 0.05 | 0.915 | 0.821 | 1.162 | Wiley et al. (in press) |
| 23 | | | | | |
| 24 | | | | | |
| 25 | | | | | |
| 26 | 0.3 ± 0.01 | 0.04 | 0.7 | 0.37 | |
| 27 | 83.2 ± 1.4 | 20 | 14 | 21 | |
| 28 | | | | | |
| 29 | | | | | |
| 30 | | | | | |
| 31 | 342 ± 22.4 | 36% @ 30 | 23% @ 30 | neg 0.9 @ 30 | Wiley et al. (in press) |
| 32 | 911 ± 116 | neg 1.9 @ 30 | 30% @ 30 | neg 0.6 @ 30 | Wiley et al. (in press) |
| 33 | >10,000 | | | | Wiley et al. (in press) |
| 34 | 23 ± 2.1 | neg 19.0 @ 30 | 5.1 @ 30 | 0.5 @ 30 | Wiley et al. (in press) |
| 35 | 111 ± 7.8 | 42.9 @ 30 | 8.2% @ 30 | 0 @ 30 | Wiley et al. (in press) |
| 36 | 465.6 ± 110 | 4 @ 30 | 6 @ 30 | 1 @ 30 | Wiley et al. (in press) |
| 37 | | neg. 17.7% @ 30 | 9.0% @ 30 | neg 0.4 @ 30 | Wiley et al. (in press) |
| 38 | 161.48 ± 24.31 | | | | Wiley et al. (in press) |
| 39 | 105.36 ± 18.06 | | | | Wiley et al. (in press) |
| 40 | 857.67 ± 42.97 | | | | Wiley et al. (in press) |
| 41 | 63.83 ± 8.21 | | | | Wiley et al. (in press) |
| 42 | 125.53 ± 12.45 | | | | Wiley et al. (in press) |
| 43 | 1772.7 ± 183.7 | | | | Wiley et al. (in press) |
| 44 | 345.7 ± 48.8 | | | | Wiley et al. (in press) |
| 45 | 190.3 ± 12.0 | | | | Wiley et al. (in press) |
| 46 | 1561.3 ± 69.7 | | | | Wiley et al. (in press) |
| 47 | 3352 ± 253.2 | | | | |
| 48 | 100.67 ± 13.88 | | | | Wiley et al. (in press) |
| 49 | 1065 ± 107.08 | | | | Wiley et al. (in press) |
| 50 | 124.93 ± 14.40 | | | | Wiley et al. (in press) |
| 51 | 11.04 ± 2.18 | | | | |
| 52 | >10,000 | | | | Wiley et al. (in press) |
| 53 | >10,000 | | | | |
| 54 | >10,000 | | | | |

What is claimed is:

1. A compound of general formula I

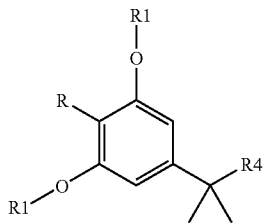

wherein:

R is a heterocyclic ring;

R1 is independently selected at each occurrence from the group consisting of hydrogen and $C_{1-6}$ alkyl;

R4 is selected from the group consisting of $C_{1-10}$ alkyl and alkenyl;

or a pharmaceutically acceptable salt thereof.

2. A compound as claimed in claim 1 wherein R is cyclothioalkyl.

3. A compound as claimed in claim 2 wherein R is selected from the group consisting of tetrahydrothiopyranyl, tetrahydrothiophen-3-yl, tetrahydropyranyl.

4. A compound as claimed in claim 1 wherein R1 is hydrogen or methyl.

5. A compound as claimed in claim 1 wherein R4 is linear $C_{5-7}$ alkyl.

6. A compound as claimed in claim 5, wherein R4 is hexyl.

7. A composition comprising a compound of formula I, together with a pharmaceutically acceptable carrier and/or excipient.

8. A composition comprising a compound of formula I together with a pharmaceutically acceptable carrier.

9. A composition comprising a compound of formula I as claimed as claim 1 together with a pharmaceutically acceptable excipient.

10. A composition comprising a compound of formula I as claimed in claim 1 selected from the group consisting of a compound of formula I with a pharmaceutically acceptable carrier a compound of formula I with a pharmaceutically acceptable diluent a compound of formula I with a pharmaceutically acceptable carrier and diluent wherein the composition is sterile and non-pyrogenic.

11. A compound as claimed in claim 1 wherein the compound is in a form selected from the group consisting of salts, esters and tautomers of the compound of formula I.

* * * * *